US006238430B1

(12) United States Patent
Klumb et al.

(10) Patent No.: US 6,238,430 B1
(45) Date of Patent: May 29, 2001

(54) CATHETER ASSEMBLY WITH CONTROLLED RELEASE ENDOLUMINAL PROSTHESIS AND METHOD FOR PLACING

(75) Inventors: Katherine J. Klumb, Los Altos; Thomas J. Fogarty, Portola Valley; Kirti P. Kamdar, Sunnyvale; Bradley B. Hill, Portola Valley, all of CA (US)

(73) Assignee: Vascular Architects, Inc., San Jose, CA (US)

( * ) Notice: Subject to any disclaimer, the term of this patent is extended or adjusted under 35 U.S.C. 154(b) by 0 days.

(21) Appl. No.: 09/400,952

(22) Filed: Sep. 22, 1999

Related U.S. Application Data

(63) Continuation-in-part of application No. 09/258,542, filed on Feb. 26, 1999.

(51) Int. Cl.[7] ........................................................ A61F 2/06
(52) U.S. Cl. ........................ 623/1.11; 623/1.13; 606/108
(58) Field of Search .................................. 606/108, 191, 606/192, 194, 198; 604/96, 101, 103, 171, 264, 286; 623/1.11, 1.12, 1.13, 1.1, 1.23

(56) References Cited

U.S. PATENT DOCUMENTS

| 3,993,078 | 11/1976 | Bergentz et al. ................. 128/334 R |
| 4,553,545 | 11/1985 | Maass et al. .......................... 128/341 |
| 4,665,918 | 5/1987 | Garza et al. ........................... 128/343 |

(List continued on next page.)

FOREIGN PATENT DOCUMENTS

| 297 21 310 | 2/1998 | (DE) . |
| 627 201 A1 | 6/1993 | (EP) . |
| 893 108 A2 | 1/1999 | (EP) . |
| WO 94/16629 | 8/1994 | (WO) . |
| WO 94/22379 | 10/1994 | (WO) . |
| WO 97/07756 | 3/1997 | (WO) . |
| 98/22159 | 5/1998 | (WO) . |
| 98/47447 | 10/1998 | (WO) . |
| 98/57692 | 12/1998 | (WO) . |

*Primary Examiner*—Gene Mancene
*Assistant Examiner*—Michael B. Priddy
(74) *Attorney, Agent, or Firm*—James F. Hann; Haynes & Beffel LLP

(57) ABSTRACT

A catheter assembly includes a coiled endoluminal prosthesis (122, 190, 198) and a catheter (136) having at least first and second telescoping shafts (138, 140, 142). The prosthesis is releasably engaged to the distal ends (144, 146, 148) of the telescoping shafts. The prosthesis is capable of assuming a second, expanded diameter state from a first, reduced diameter state. The length and number of turns (128) of the coiled prosthesis can be changed by the relative translation and rotation of the shafts. The catheter assembly is especially useful for placing a coiled stent graft (122), in which one turn (132, 134) of the prosthesis has a greater pitch than the adjacent turns, at the intersection (184) of a bifurcation within a blood vessel (182). Remotely viewable marker elements (188, 190, 191, 192, 193, 195, 197) may be used and include a marker element (193, 190A, 197) configured to indicate orientation as well as axial position of the prosthesis. The ends of the prosthesis may be substantially less stiff than the remainder of the prosthesis and/or shaped to help prevent tissue trauma.

46 Claims, 16 Drawing Sheets

U.S. PATENT DOCUMENTS

| | | | |
|---|---|---|---|
| 4,732,152 | 3/1988 | Wallsten et al. | 128/343 |
| 4,760,849 | 8/1988 | Kropf | 128/341 |
| 4,795,458 | 1/1989 | Regan | 623/1 |
| 4,848,343 | 7/1989 | Wallsten et al. | 128/343 |
| 4,875,480 | 10/1989 | Imbert | 128/343 |
| 4,886,062 | 12/1989 | Wiktor | 128/343 |
| 4,913,141 | 4/1990 | Hillstead | 606/108 |
| 5,037,427 | 8/1991 | Harada et al. | 606/108 |
| 5,147,370 | 9/1992 | McNamara et al. | 606/108 |
| 5,201,757 | 4/1993 | Heyn et al. | 606/198 |
| 5,246,445 | 9/1993 | Yachia et al. | 606/108 |
| 5,306,294 | 4/1994 | Winston et al. | 623/1 |
| 5,360,401 | 11/1994 | Turnland | 604/96 |
| 5,372,600 | 12/1994 | Beyar et al. | 606/108 |
| 5,411,551 | 5/1995 | Winston et al. | 623/1 |
| 5,443,500 | 8/1995 | Sigwart | 623/1 |
| 5,476,505 | 12/1995 | Limon . | |
| 5,607,445 | 3/1997 | Summers | 606/198 |
| 5,683,451 | 11/1997 | Lenker et al. | 623/1 |
| 5,749,919 | 5/1998 | Blanc . | |
| 5,776,142 | 7/1998 | Gunderson . | |
| 5,797,952 | 8/1998 | Klein | 606/198 |
| 5,824,052 | 10/1998 | Khosravi et al. . | |
| 5,824,053 | 10/1998 | Khosravi et al. | 623/1 |
| 5,836,966 | 11/1998 | St. Germain . | |
| 6,027,516 | 2/2000 | Kolobow et al. . | |

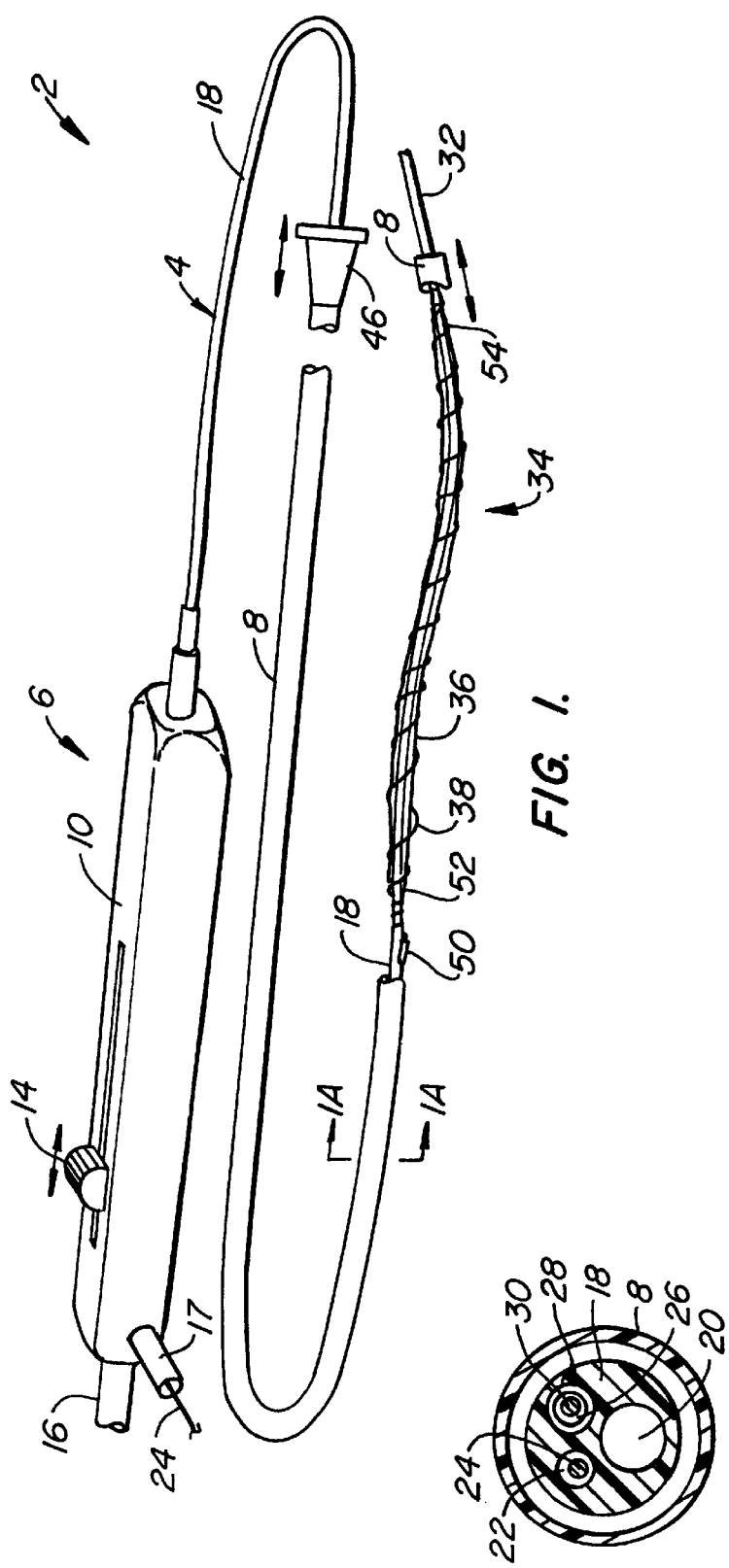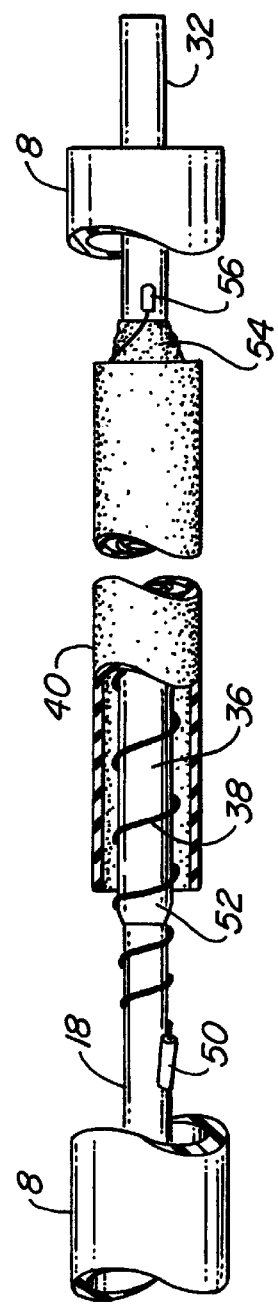

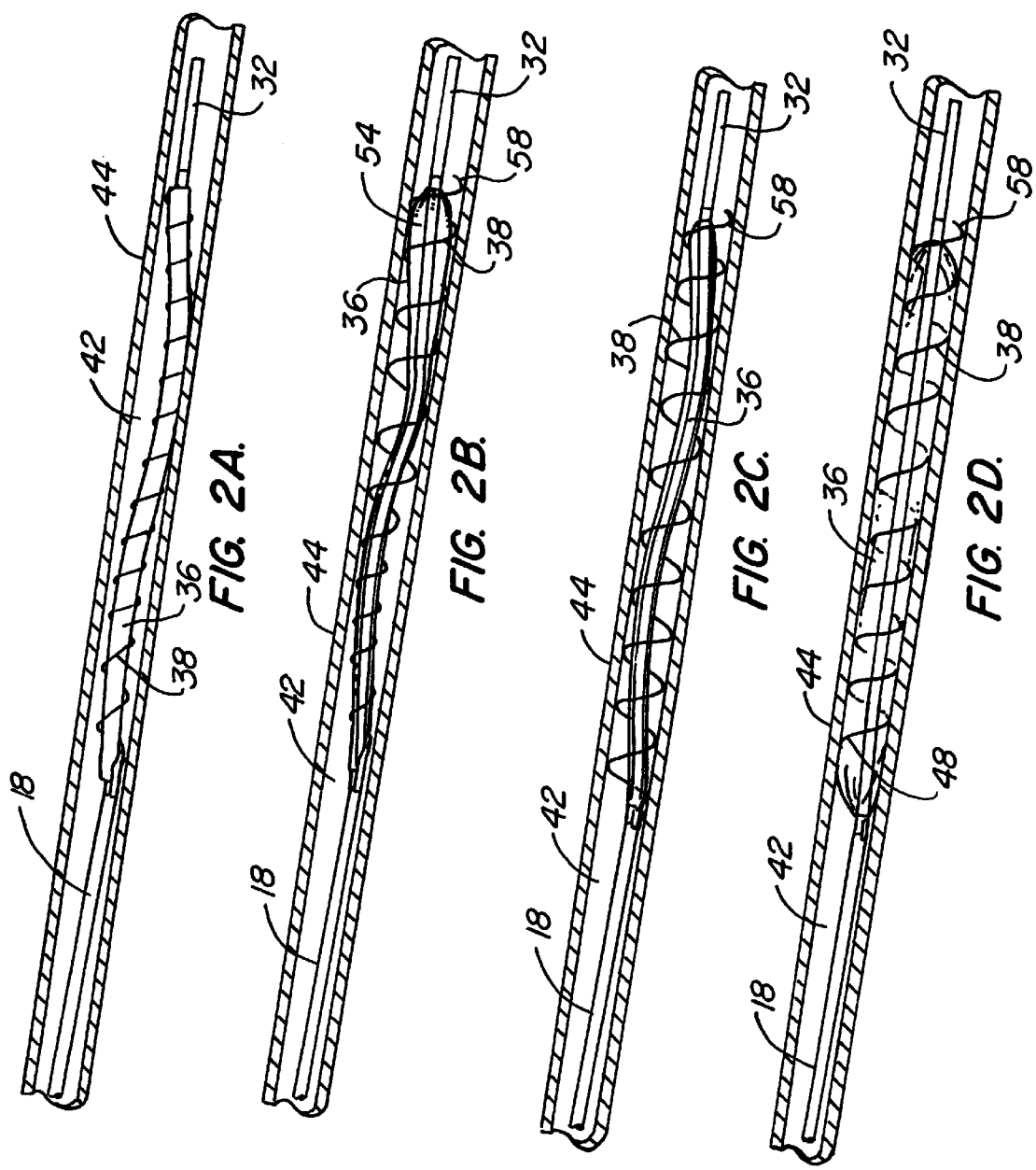

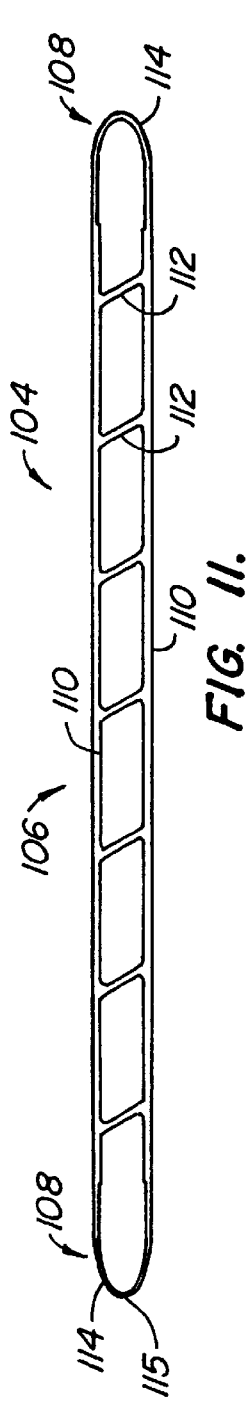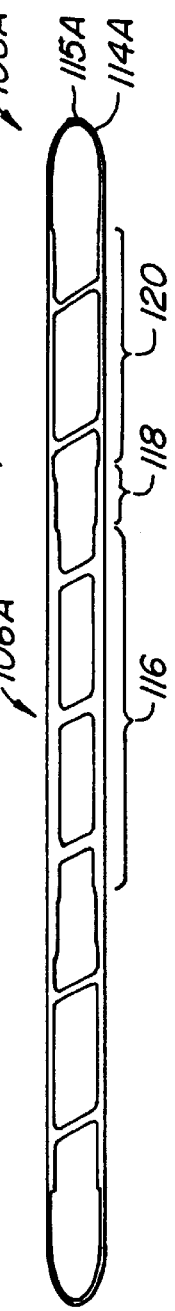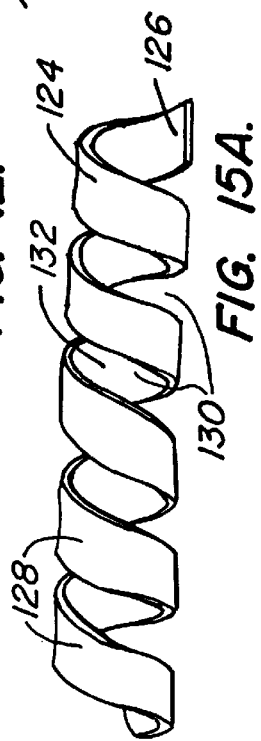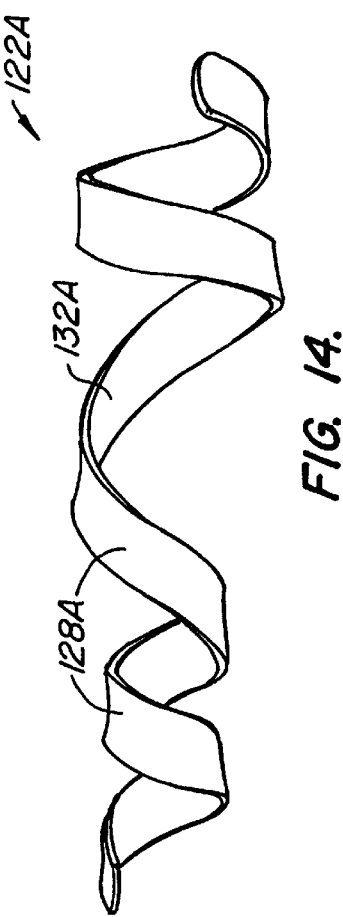

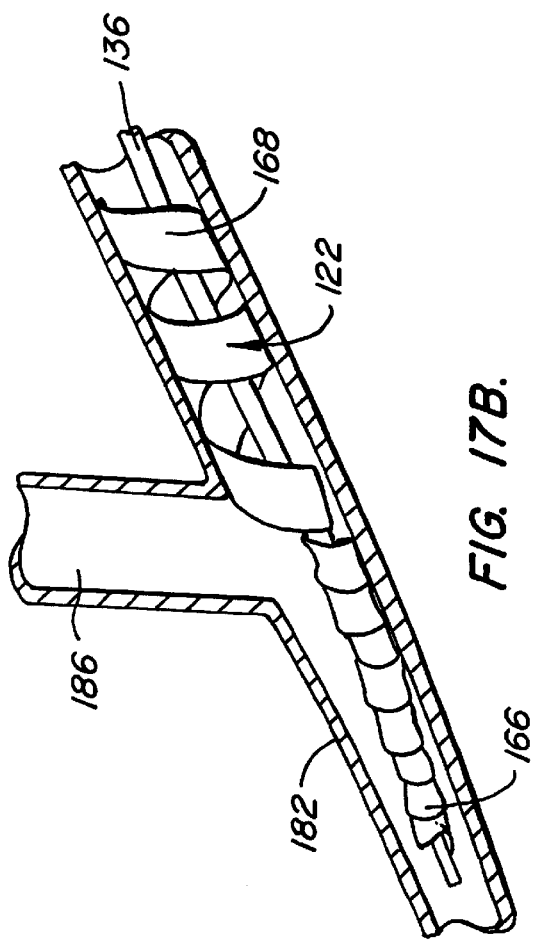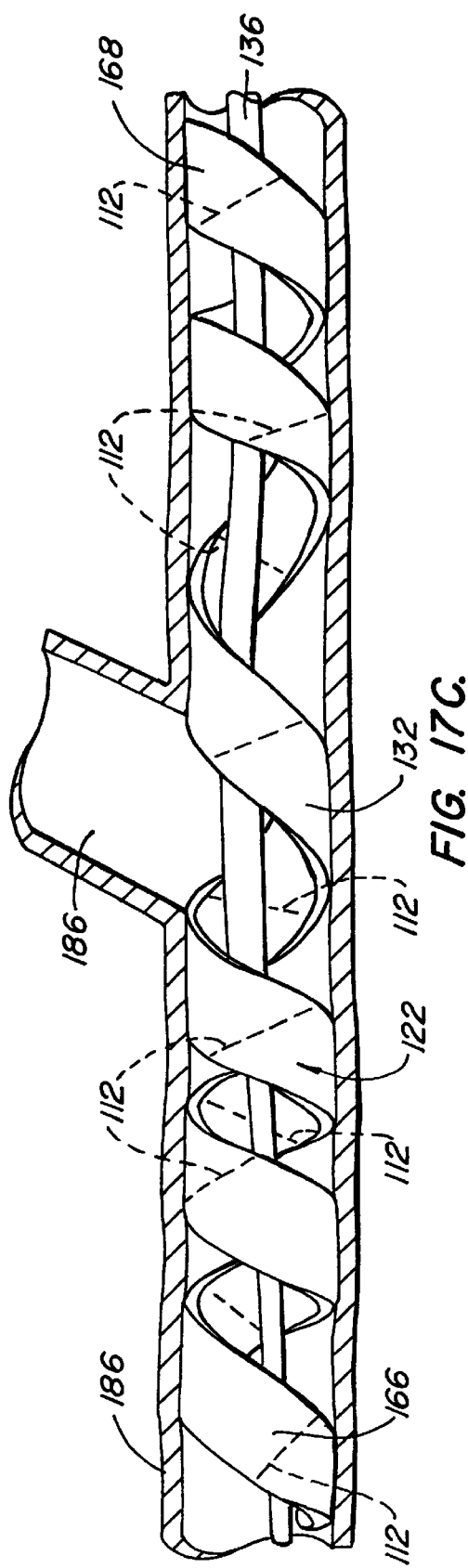

CATHETER ASSEMBLY WITH CONTROLLED RELEASE ENDOLUMINAL PROSTHESIS AND METHOD FOR PLACING

CROSS-REFERENCE TO RELATED APPLICATIONS

This is a continuation-in-part of U.S. patent application No. 09/258,542 filed Feb. 26, 1999. This is related to U.S. patent application No. 09/400,955 entitled Endoluminal Prosthesis, filed on the same day as this application.

BACKGROUND OF THE INVENTION

The present invention provides devices and methods for the endoluminal placement of prostheses, particularly within the vascular system for the treatment of cardiovascular disease, such as vascular stenoses, dissections, aneurysms, and the like. The apparatus and methods, however, are also useful for placement in other body lumens, such as the ureter, urethra, biliary tract, gastrointestinal tract and the like, for the treatment of other conditions which may benefit from the introduction of a reinforcing or protective structure within the body lumen. The prostheses will be placed endoluminally. As used herein, "endoluminally" will mean placement by percutaneous or cutdown procedures, wherein the prosthesis is transluminally advanced through the body lumen from a remote location to a target site in the lumen. In vascular procedures, the prostheses will typically be introduced "endovascularly" using a catheter over a guidewire under fluoroscopic guidance. The catheters and guidewires may be introduced through conventional access sites to the vascular system, such as through the femoral artery, or brachial and subclavian arteries, for access to the target site.

An endoluminal prosthesis typically comprises at least one radially expansible, usually cylindrical, body segment. By "radially expansible," it is meant that the body segment can be converted from a small diameter configuration (used for endoluminal placement) to a radially expanded, usually cylindrical, configuration which is achieved when the prosthesis is implanted at the desired target site. The prosthesis may be non-resilient, e.g., malleable, thus requiring the application of an internal force to expand it at the target site. Typically, the expansive force can be provided by a balloon catheter, such as an angioplasty balloon for vascular procedures. Alternatively, the prosthesis can be self-expanding. Such self-expanding structures are provided by a temperature-sensitive superelastic material, such as Nitinol, which naturally assumes a radially expanded condition once an appropriate temperature has been reached. The appropriate temperature can be, for example, a temperature slightly below normal body temperature; if the appropriate temperature is above normal body temperature, some method of heating the structure must be used. Another type of self-expanding structure uses resilient material, such as a stainless steel or superelastic alloy, and forming the body segment so that it possesses its desired, radially-expanded diameter when it is unconstrained, e.g., released from radially constraining forces a sheath. To remain anchored in the body lumen, the prosthesis will remain partially constrained by the lumen. The self-expanding prosthesis can be delivered in its radially constrained configuration, e.g. by placing the prosthesis within a delivery sheath or tube and retracting the sheath at the target site. Such general aspects of construction and delivery modalities are well-known in the art and do not comprise part of the present invention.

The dimensions of a typical endoluminal prosthesis will depend on its intended use. Typically, the prosthesis will have a length in the range from 0.5 cm to 10 cm, usually being from about 0.8 cm to 5 cm, for vascular applications. The small (radially collapsed) diameter of cylindrical prostheses will usually be in the range from about 1 mm to 10 mm, more usually being in the range from 1.5 mm to 6 mm for vascular applications. The expanded diameter will usually be in the range from about 2 mm to 42 mm, preferably being in the range from about 3 mm to 15 mm for vascular applications.

One type of endoluminal prosthesis includes both a stent component and a graft component. These endoluminal prostheses are often called stent grafts. A stent graft is typically introduced using a catheter with both the stent and graft in contracted, reduced-diameter states. Once at the target site, the stent and graft are expanded. After expansion, the catheter is withdrawn from the vessel leaving the stent graft at the target site.

Grafts are used within the body for various reasons, such as to repair damaged or diseased portions of blood vessels such as may be caused by injury, disease, or an aneurysm. It has been found effective to introduce pores into the walls of the graft to provide ingrowth of tissue onto the walls of the graft. With larger diameter grafts, woven graft material is often used. In small diameter vessels, porous fluoropolymers, such as PTFE, have been found useful.

Coil-type stents can be wound about the catheter shaft in torqued compression for deployment. The coil-type stent can be maintained in this torqued compression condition by securing the ends of the coil-type stent in position on a catheter shaft. The ends are released by, for example, pulling on wires once at the target site. See, for example, U.S. Pat. Nos. 5,372,600 and 5,476,505. Alternatively, the endoluminal prosthesis can be maintained in its reduced-diameter condition by a sleeve; the sleeve can be selectively retracted to release the prosthesis. A third approach is the most common. A balloon is used to expand the prosthesis at the target site. The stent is typically extended past its elastic limit so that it remains in its expanded state after the balloon is deflated. One balloon expandable stent is the PALMAZ-SHATZ stent available from the CORDIS Division of Johnson & Johnson. Stents are also available from Arterial Vascular Engineering of Santa Rosa, Calif. and Guidant Corporation of Indianapolis, Ind.

SUMMARY OF THE INVENTION

The present invention is directed to a catheter assembly including an endoluminal prosthesis, such as a stent, a graft, a stent graft or other endoluminal structure, and a catheter having at least first and second telescoping shafts to which the prosthesis is releasably engaged. The distal end portions of the telescoping shafts include prosthesis portion holders. The prosthesis is capable of assuming a second, expanded diameter state from a first, reduced diameter state and is releasably engagable with the first and second prosthesis portion holders. The catheter assembly is especially useful for placing the endoluminal prosthesis at the intersection of a bifurcation within a blood vessel.

The prosthesis may be a coiled stent graft in which one turn of the prosthesis has a greater pitch than the adjacent turns. This permits substantially unrestricted fluid flow between a first vessel housing the prosthesis and a branching vessel when the prosthesis is properly placed with the at least one turn at the intersection of the first and branching vessels.

When the at least one turn is at an end of the prosthesis the prosthesis can be properly placed using only the first and second telescoping shafts. When the at least one turn is at a central portion of the prostheses, it is preferred that the catheter shaft include a third telescoping and rotatable shaft which can also releasably engage the prosthesis. The prosthesis is typically engaged at each end and at the at least one turn by the prosthesis engaging portions of the shafts.

The prosthesis and/or the catheter shaft may also include remotely viewable marker elements at spaced apart positions. At least one of the marker elements is preferably located at the at least one turn, so to aid proper placement of the prosthesis at the intersection of the first and branching vessels. One or more of the marker elements may be configured to indicate orientation as well as axial position.

The ends of the prosthesis are preferably substantially less stiff than the remainder of the prosthesis. This provides several advantages. It tends to cause the ends of the prosthesis to open up first in the center and then at the end areas to reduce abrasion of the vessel walls by the ends. Also, by the ends being less stiff than the remainder of the prosthesis, injury to the vessel walls is less likely. Also, the end portions of the prosthesis may have an inwardly-tapering portion with a blunt tip, again to help prevent tissue trauma.

A further aspect of the invention relates to a method for placing an endoluminal prosthesis within a body. The method includes introducing the distal portion of a catheter assembly at a chosen position within the body. The distal portion includes a coiled stent graft wound about a catheter shaft and capable of assuming a second, expanded-diameter state from a first, reduced-diameter state. The turns of the stent graft have spaces therebetween when in the second state. The pitch of at least one turn is greater than the pitch of adjacent turns. The stent graft is releasably connected to the catheter shaft at first and second positions along the stent graft. The first position is at the at least one turn. The at least one turn is then located at an intersection of a first vessel and a branching vessel. The second position of the stent graft is then released from the catheter to permit at least a portion of the stent graft to expand while maintaining the first position of the stent graft at the intersection. The remainder of the stent graft, including the first portion, is then released permitting the remainder of the stent graft to expand. When the at least one turn is at a central position of the stent graft, the central position is preferably released after ends have been released.

It is preferred that the introducing step be carried out using a catheter shaft including first and second rotatable, telescoping shafts with the first and second positions of the stent graft releasably connected to the first and second telescoping shafts. This permits the telescoping shafts to be longitudinally moved relative to one another to selectively change the length of the stent graft or rotated relative to one another to selectively change the number of turns of the stent graft.

If desired more than one stent graft can be used along the first vessel or along a branching vessel or both. The stent graft may have different diameters when in the second, expanded state to accommodate different diameters within a vessel.

Other features and advantages of the invention will appear from the following description in which the preferred embodiments have been set forth in detail in conjunction with the accompanying drawings.

BRIEF DESCRIPTION OF THE DRAWINGS

FIG. 1 is an overall view of a catheter assembly using a straight stent embodiment;

FIG. 1A is an enlarged cross-sectional view taken along line 1A—1A of FIG. 1;

FIG. 1B is an enlarged simplified partial cross-sectional view of the distal portion of the catheter of FIG. 1, with the addition of a general tubular external graft, to illustrate the relative relationship between the various components;

FIG. 2A illustrates the catheter of FIG. 1A introduced into a blood vessel at a target site after the sheath has been pulled back to expose the stent and balloon at the target site, the graft of FIG. 1B being omitted from FIGS. 2A–2G for clarity of illustration;

FIG. 2B is similar to FIG. 2A with the distal portion of the balloon partially inflated to cause the first, distal stent portion to disengage from the first stent portion holder;

FIG. 2C is similar to FIG. 2B but after the balloon has been deflated which permits the distal portion of the stent to spin relatively freely and thus expand to press against the inside wall of the blood vessel;

FIG. 2D illustrates the balloon fully reinflated and showing the second, proximal end of the stent disengaged from the second stent end holder;

FIG. 11 illustrates a stent blank used to create a coiled stent similar to that shown in FIG. 4E;

FIG. 12 illustrates a stent blank similar to that of FIG. 11 but having different thickness along its length;

FIG. 14 illustrates a stent graft similar to that of FIG. 13 but in which one end of the stent graft has much greater radially expanded diameter than the other portion to accommodate a vessel having different internal diameters;

FIG. 15A shows a stent graft similar to that of FIG. 13 but with generally evenly-spaced turns;

FIG. 17B illustrates the release of the proximal half of the stent graft;

FIG. 17C illustrates the release of the distal half of the stent graft prior to the removal of the catheter shafts;

DESCRIPTION OF THE SPECIFIC EMBODIMENTS

Figure 2E:
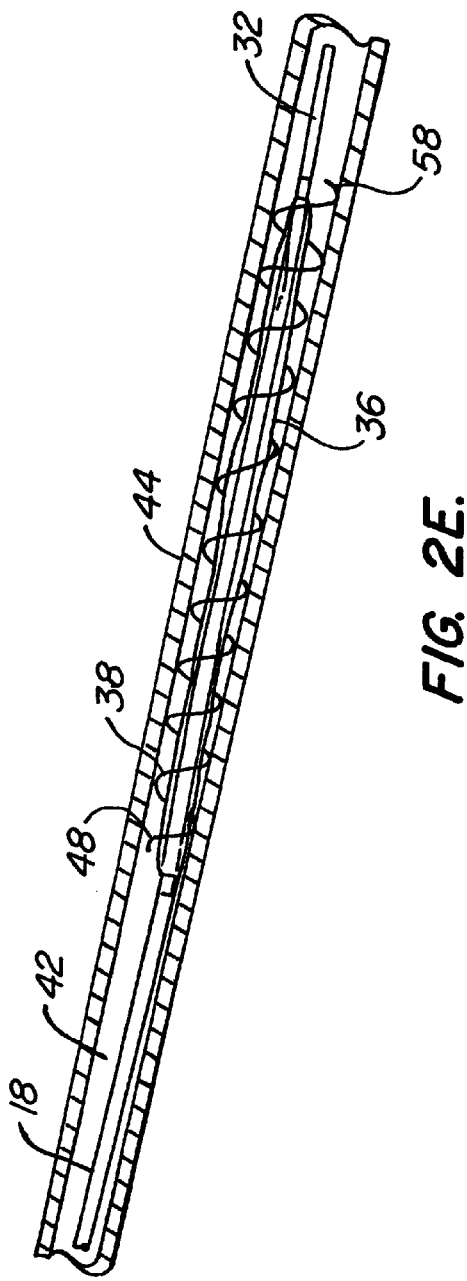
FIG. 2E is similar to FIG. 2D but with the balloon fully deflated.

FIG. 1 illustrates a catheter assembly 2 including broadly a catheter 4 extending from a proximal end adaptor 6, the catheter having an introducer sheath 8 slidably mounted over the catheter. Proximal end adaptor 6 includes a body 10 to which a push wire manipulator 14 is sidably mounted. Proximal end adaptor 6 also includes an inflation port 16, to permit a balloon, discussed below, to be inflated and deflated during use, and a guidewire port 17.

Catheter 4 includes elongate catheter shaft 18 defining three lumens therein. FIG. 1A illustrates an inflation lumen 20, coupled to inflation port 16, a guidewire lumen 22 housing a guidewire 24, the proximal end of the guidewire passing through guidewire port 17. The catheter shaft 18 also includes a push wire lumen 26 housing a push wire tube 28, a push wire 30 being housed within push wire tube 28. Push wire 30 is connected to push wire manipulator 14 and is pushed and pulled through push wire tube 28 by the movement of manipulator 14. Push wire tube 28 is used to help prevent push wire 30 from buckling, which may occur during use due to the relatively thin diameter of the push wire, typically about 0.10 to 76 mm (0.004 to 0.030 inch). The distal end of guidewire 24, not shown, is positioned near the tip 32 of catheter shaft 18 and is used to help guide tip 32 through the body, typically through blood vessels, as is conventional. During the typically percutaneous introduction of the distal portion 34 of catheter 4 into the vasculature, sheath 8 is in the distal position shown in FIG. 1 to cover up the balloon 36, stent 38, and graft 40 as shown in FIG. 1B.

Once in position at the target site 42 in blood vessel 44, see FIG. 2A, handle 46 of introducer sheath 8 is pulled in a proximal direction to expose graft 40, stent 38, and balloon 36. Note that in FIGS. 2A–2F, graft 40 is not shown for clarity of illustration.

Stent 38 is a coil-type of stent typically made of 0.10 to 0.76 mm (0.004 to 0.030 inch) diameter Nitinol wire. Stent 38 may be made of other materials including stainless steel, Elgiloy®, a cobalt-chromium-nickel alloy made by Elgiloy Inc., and polymers. Stent 38, when in a relaxed state, typically has a diameter of about 2 to 30 mm to accommodate blood vessel 44 having an internal diameter of about 2 to 30 mm. The wire diameter, coil diameter, and other properties of stent 38 may vary according to the particular body region to be accessed and the procedure to be conducted. In FIGS. 1B and 2A, balloon 36 is in a deflated condition while stent 38 is in a first, reduced-diameter state with the coil-type stent 38 in torqued compression onto catheter shaft 18 and balloon 36. Stent 38 includes a proximal end 48, shown also in FIG. 3A, which is housed within a hollow interior of a stent end holder 50. Proximal end 48 of stent 38 can be selectively dislodged from proximal stent end holder 50 by the distal movement of push wire 30 through push wire tube 28. In this embodiment, proximal stent end holder 50 is an extension of push wire tube 28 as suggested in FIG. 3A. Instead of push wire 30, push wire tube 28 could be pulled into catheter shaft 18 to release proximal end 48 of stent 38.

It may be desired that the length of stent 34 be about the same when in the reduced-diameter state as when in the relaxed, enlarged-diameter state. This is desirable to minimize shifting of the stent at the target site during deployment. The use of a coil-type stent helps to achieve this by permitting the appropriate spacing the turns of the stent onto the balloon-covered catheter shaft when in a reduced-diameter state. For example, stent 38 having a relaxed diameter of 6 mm, a relaxed length of 5 cm and 10 turns in a relaxed state, can be wound onto the balloon-covered catheter shaft to assume a reduced-diameter state with about 30 turns, a diameter of about 2.5 mm and the same length of about 5 cm. The results will vary depending on various factors, such as the pitch of the coil.

A proximal end 52 of balloon 36 is spaced-apart from stent end holder 50 by a distance sufficient to permit at least one turn, and preferably one-and-a-half to two turns, of stent 38 to be wrapped directly around catheter shaft 18 without any of balloon 38 being between stent 38 and catheter shaft 18. The purpose of this is to inhibit the dislodgment of proximal end 48 from stent end holder 50 upon the initial inflation of balloon 36 as will be discussed in more detail below. Thus, the initial turn or turns of stent 38 are in effective contact with catheter shaft 18 because there is no portion of balloon 36 between the turn or turns of the stent and the catheter shaft.

The distal end 54 of balloon 36 is positioned near the distal stent end holder 56. Accordingly, when the distal stent end 58 is engaged within distal stent end holder 56, stent 38 quickly starts wrapping around balloon 36. Thus, upon inflation of balloon 36, distal stent end 58 is pulled from distal end holder 56 as shown in FIG. 2B. Note that in FIG. 2B, balloon 36 is only partly inflated. Inflation of distal end 54 of balloon 36 is aided in this embodiment by somewhat more loosely wrapping stent 38 around the balloon at distal end 54 than over the remainder of the balloon. This reduces the resistance to inflation of the balloon at distal end 54 thus permitting the expansion of the distal end of stent 38 before expansion at its proximal end. Other ways to promote this initial expansion of distal end 54 of balloon 36, such as making distal end 54 easier to expand than the remainder of the balloon or only partially retracting sleeve 8 or using a balloon with separately inflatable proximal and distal portions, can be used.

After this partial expansion of balloon 36, the balloon is deflated as shown in FIG. 2C. This permits stent 38 to more freely expand within blood vessel 44 so that a greater portion of the stent is in its expanded state in FIG. 2C than in FIG. 2B. FIG. 2D illustrates balloon 36 after having been fully inflated and the dislodgment of proximal end 48 of stent 38 from proximal end stent holder 50 by moving push wire 30 distally through the manipulation of push wire manipulator 14. This dislodgment of proximal end 48 preferably occurs after the full inflation of balloon 36; it could also occur before the full inflation of the balloon as well.

Figure 2F:
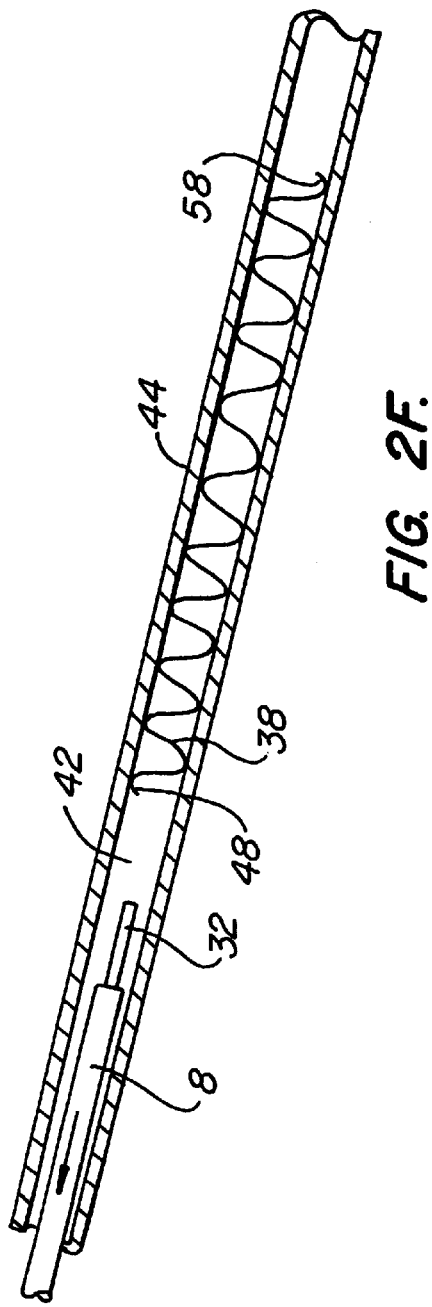
FIG. 2F shows the stent in its second, expanded-diameter state after withdrawal of the distal portion of the catheter shaft.
Figure 4A:
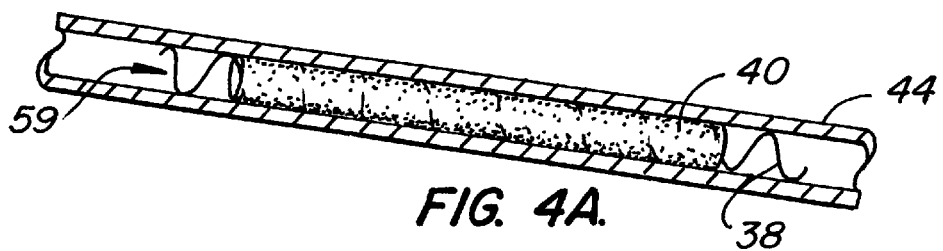
FIG. 4A illustrates the stent of FIG. 2G with the external graft of FIG. 1B surrounding the stent and held against the inner wall of the blood vessel by the stent.

FIG. 2E illustrates balloon 36 deflated leaving stent 38 in its expanded-diameter state pressing graft 40, not shown in FIGS. 2A–2F but shown in FIG. 4A, against the inner wall of blood vessel 44. Though not always necessary, it may be desired to move sheath 40 in a distal direction to cover balloon 36 prior to removing the distal portion of the catheter shaft. FIG. 2F illustrates stent 38 in its expanded-diameter state after removal of catheter shaft 18 and sheath 8. It can be noted that in FIGS. 1B and 4A the length of graft 40 is shorter than the length of stent 38; this helps to ensure that the ends of graft 40 are pressed against the interior of blood vessel 44.

In use, the user introduces distal portion 34 of catheter 4 into, for example, a suitable blood vessel 44 and directs tip 32 of catheter shaft 18 to a target site 42 using guidewire manipulator 12 and appropriate visualization techniques as is conventional. Balloon 36 is partially inflated through inflation port 16 to the condition of FIG. 2B causing distal stent end 58 to be dislodged from distal stent end holder 56. Balloon 36 is then deflated to permit a distal portion of stent 38 to more fully expand within blood vessel 44. Balloon 36 is then fully expanded as shown in FIG. 2D and push wire 30 is extended by moving push wire manipulator 14 in a distal direction causing proximal end 48 of stent 36 to be dislodged from proximal stent end holder 50; alternatively, push wire 30 could be extended to first dislodge proximal end 48 of stent 38B from proximal end stent holder 50 and then balloon 36 could be fully expanded. The inflation of balloon 36 also expands graft 40. Balloon 36 is then deflated as shown in FIG. 2E and withdrawn into sheath 8. A distal portion of catheter shaft 18 and balloon 36 therewith are then withdrawn from target site 42 in blood vessel 44 (see FIG. 2F) leaving stent 38 and graft 40, which together constitute a stent graft 59, in place as shown in FIG. 4A.

Figure 4B:
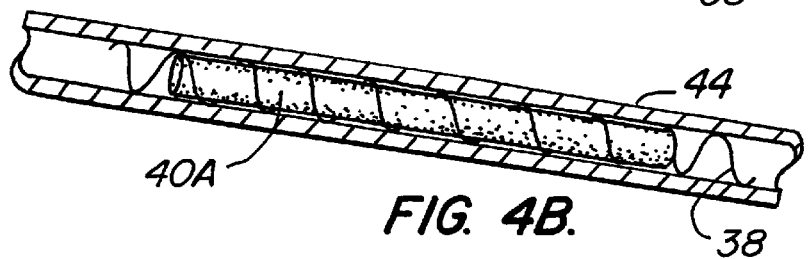
FIG. 4B illustrates the stent of FIG. 2G with an internal graft.

FIG. 4B illustrates an alternative embodiment in which graft 40A is an internal graft coupled to stent 38. One method of coupling internal graft 40A to stent 38 is through the use of one or more strips 60 of graft material. Pockets, not shown, are created between stent 40A and strips 60 to permit stent 38 to pass between the two. The gaps are relatively large to prevent graft 40A from being overly deformed during the deployment of the stent and graft.

Figure 4D:
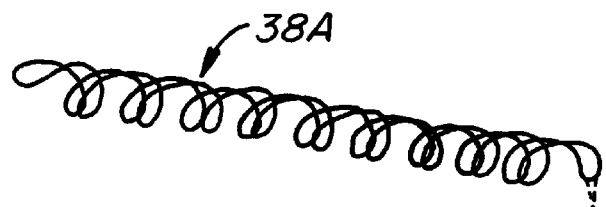
FIG. 4D illustrates an alternative coil-type stent in which the stent comprises a pair of spaced-apart coiled stent wires.

FIG. 4D illustrates a stent 38A made up of a pair of spaced-apart coiled stent wires joined together at their ends. To permit the ends of stent 38 to be secured to catheter shaft 18, the stent end holders could, for example, be modified to accommodate the generally U-shaped ends or the ends could be squeezed together or otherwise made to form a pointed end as suggested by the dashed lines at one end of stent end 38A.

Figure 4E:
FIG. 4E illustrates a stent graft in which parallel stent wires are kept in a spaced-apart relationship by spacers, the coiled stent wires being covered on both the inside and the outside by graft material, only a portion of the stent of FIG. 4A shown covered by the graft material to illustrate the arrangement of the coiled stent wires and spacers.
Figure 4C:
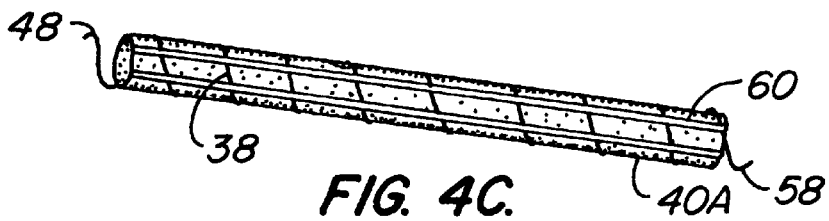
FIG. 4C illustrates fastening an internal graft to an external stent using strips of graft material creating pathways for the stent.

FIG. 4E illustrates a presently preferred embodiment in which a stent 38B is made up of a pair of coiled stent wires 62 joined together and maintained in a spaced-apart relationship by spacer wires 64 to create a ladder-like stent 38B. A strip 66 of graft material is secured to coiled stent wire 62 to form a spiral graft 40B surrounding stent 38B to lie on both the inside and the outside of the stent. Only a portion of stent 38B is covered with strip 66 to illustrate the construction of the stent. Strip 66 of graft material can be adhered to stent 38B in a variety of ways including use of an adhesive, heat welding, or making strip 66 in the form of a tube or a double-sided strip with a hollow interior which encases coiled stent wires 62. It can be seen that only one of the two coiled stent wires 62 extend outwardly at each end of stent 38B to form the proximal end 48B and the distal end 58B of stent 38B.

Ladder-like stent 38B could also be made from a tube or sheet of stent material by, for example, stamping, laser cutting, waterjet cutting or other suitable processes. It is expected that processes which do not overly heat the stent material, such as waterjet cutting, may be preferred. The graft material can be in the form of a tube of graft material which is slid over ladder-like stent 38B and secured in place by, for example, suturing the ends of the graft material.

Figure 5:
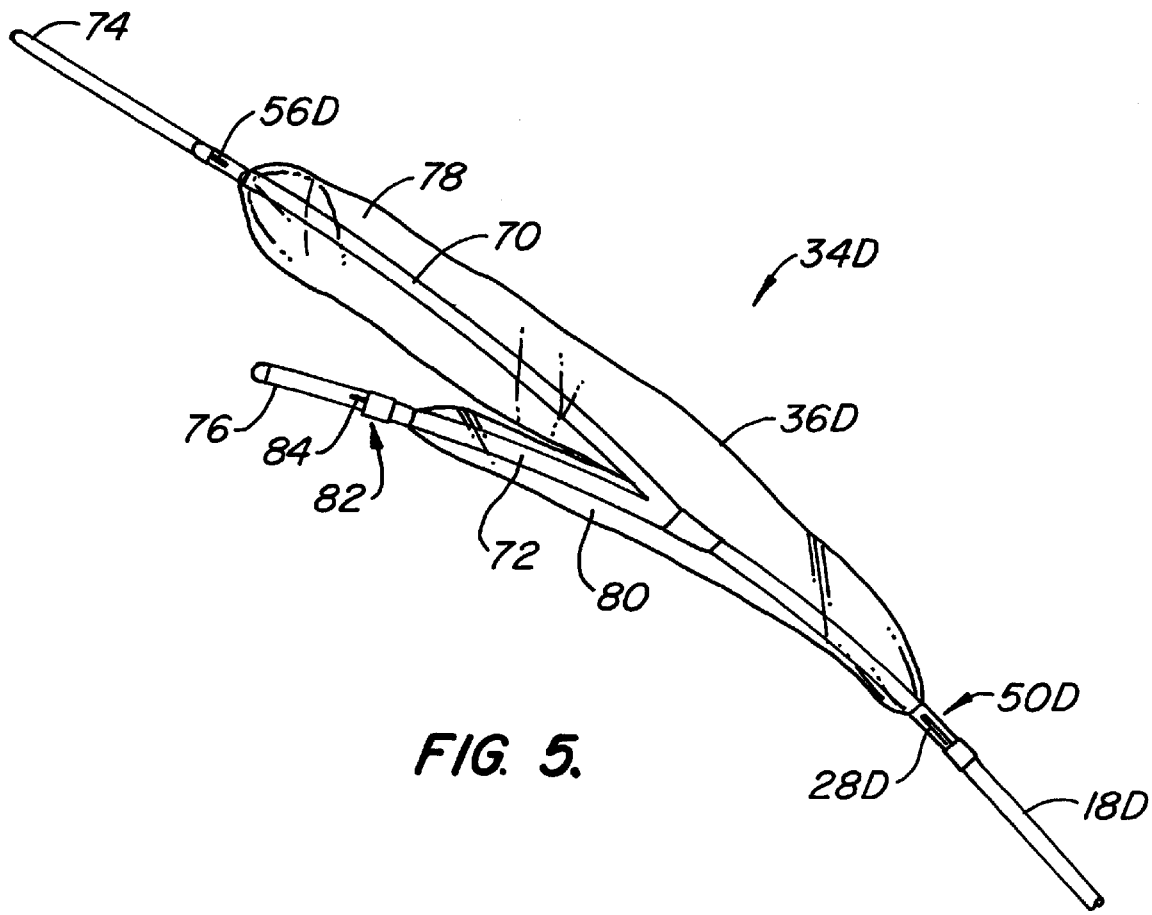
FIG. 5 shows a bifurcated version of the catheter and balloon allowing for deployment of a bifurcated prosthesis, the prosthesis not shown.

FIG. 5 shows a distal portion 34D of a bifircated catheter made according to the invention with like reference numerals referring to like elements. Catheter shaft 18D includes first and second arms 70, 72 terminating at first and second tips 74, 76. In FIG. 5 neither a stent, shown in FIG. 6, nor graft material is illustrated for clarity of illustration. Balloon 36D is a bifurcated balloon having a first portion 78 extending along first arm 70 and a second portion 80 extending along second arm 72. Proximal stent end holder 50 is carried on catheter shaft 50D while distal stent end holder 56D is positioned along first arm 70D. The stent end holders 50D, 56D are similar to stent end holders 50, 56 illustrated in FIGS. 3A and 3B with the hollow tubular members extending distally for proximal stent end holder 50 and proximally for distal stent end holder 56D. A second distal stent end holder 82 is carried along second arm 72 and has a distally extending open-ended tube 84 corresponding to push wire tube 28D in that it also extends in a distal direction and uses a push wire to disengage the end of a stent from within the push wire tube 84. As discussed above, other methods for removing the ends of the stents from push wire tubes 28D, 84 such as retracting the push wire tubes proximally, could also be used.

Figure 3A:
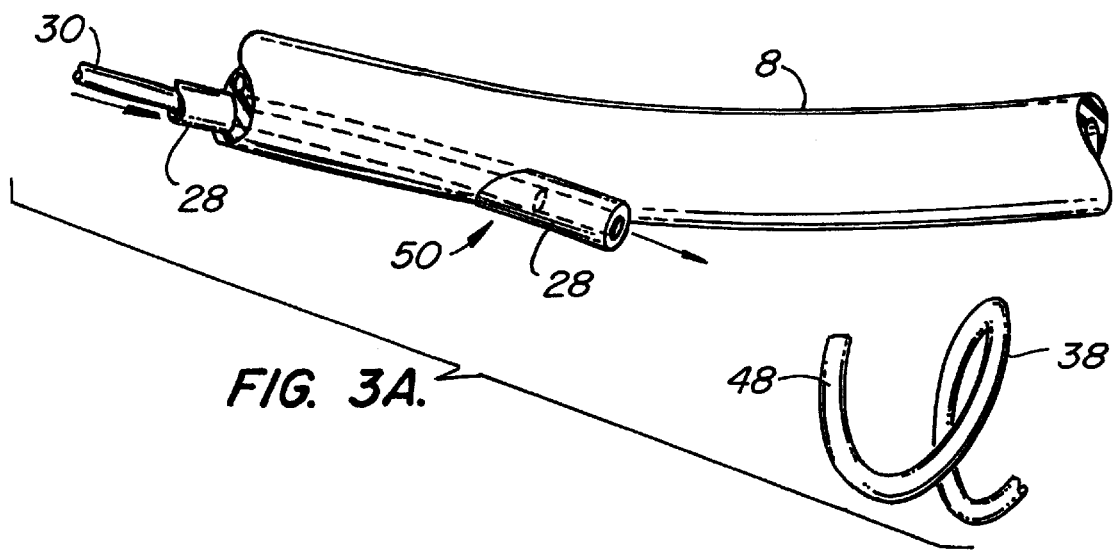
FIG. 3A is an enlarged view illustrating a push wire extending along the catheter shaft, passing through a push wire tube to permit the second, proximal end of the stent to be disengaged from the catheter shaft.
Figure 3B:
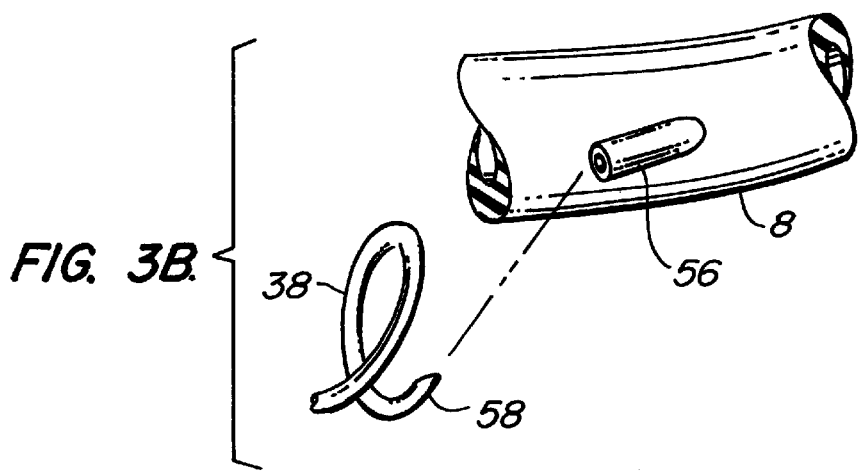
FIG. 3B illustrates the first stent end holder and the first, distal end of the stent which slidably engages an opening formed in the first stent end holder.
Figure 6:
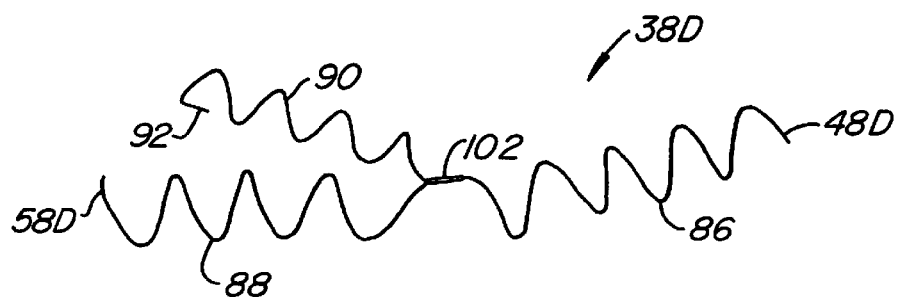
FIG. 6 illustrates a bifurcated stent.

FIG. 6 illustrates a bifurcated stent 38D having a main portion 86 and first and second arms 88, 90 which are wrapped around main portion of catheter shaft 18D and first and second arms 70, 72 respectively. Arm 88 is an extension of main portion 86; arm 90 is joined to arm 88 and main portion 86 at junction 102. Proximal end 48D of stent 38D corresponds to proximal end 48 of stent 38 as shown in FIG. 3A while distal end 58D of stent 38D corresponds to distal stent end 58 of stent 38 shown in FIG. 3D. Proximal and distal ends 48D, 58D engage proximal and distal stent end holders 50D, 56D in manner similar to those of FIGS. 3A and 3B. However, the distal end 92 of second arm 90 may have a reverse bend.

Figure 7:
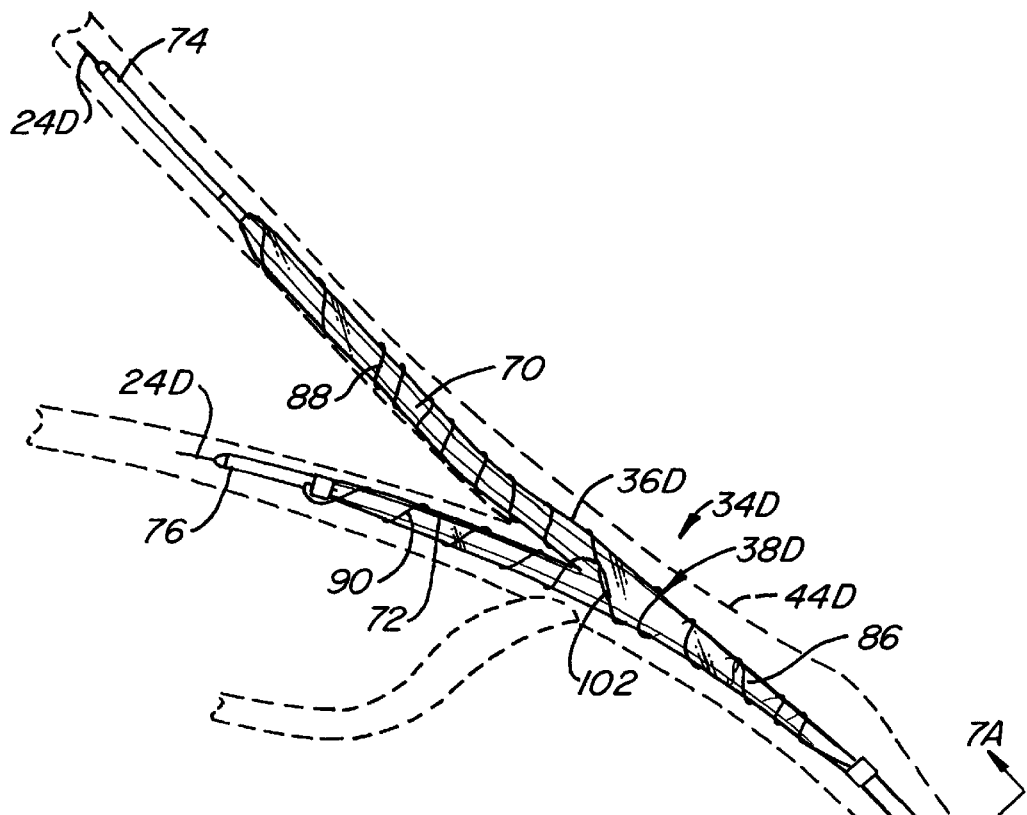
FIG. 7 shows the bifurcated stent of FIG. 6 loaded onto the bifurcated catheter of FIG. 5 with the balloon deflated.
Figure 7A:
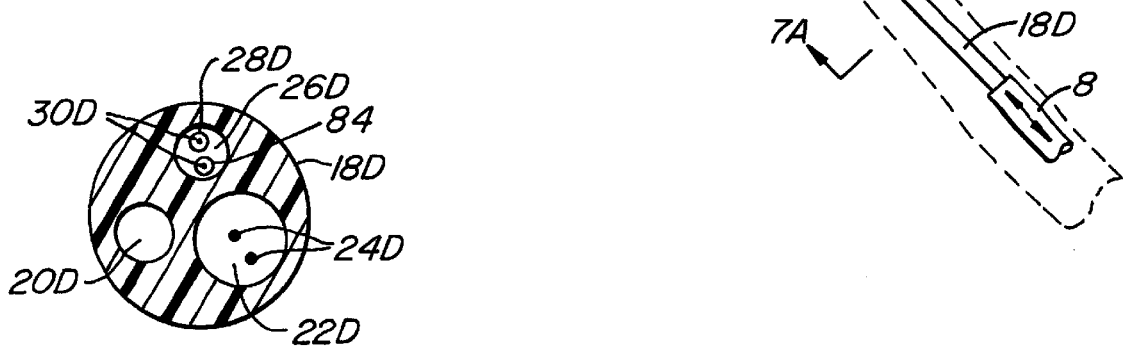
FIG. 7A is an enlarged cross sectional view taken along line 7A—7A of FIG. 7.

As shown in FIG. 7A, catheter shaft 18D defines three lumens, inflation lumen 20D, guidewire lumen 22D, housing tube guidewires 24D, one for each arm 70, 72, and a push wire lumen 26D housing push wire tubes 28, 84 with push wires 30D slidingly passing within the push wire tubes 28D, 84.

Figure 8:
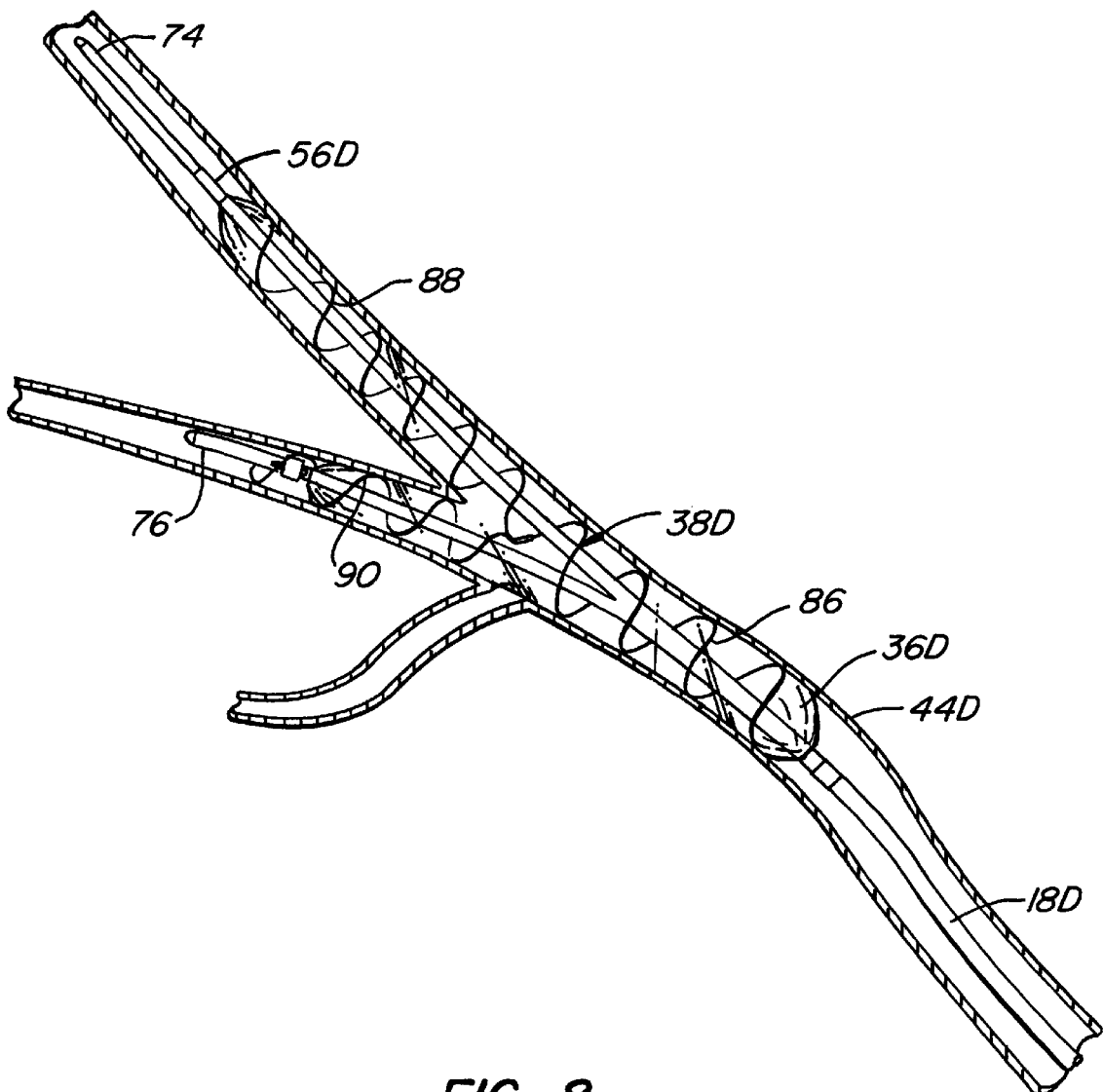
FIG. 8 shows the bifurcated stent of FIG. 7 deployed in a bifurcated vessel with the balloon inflated.
Figure 9:
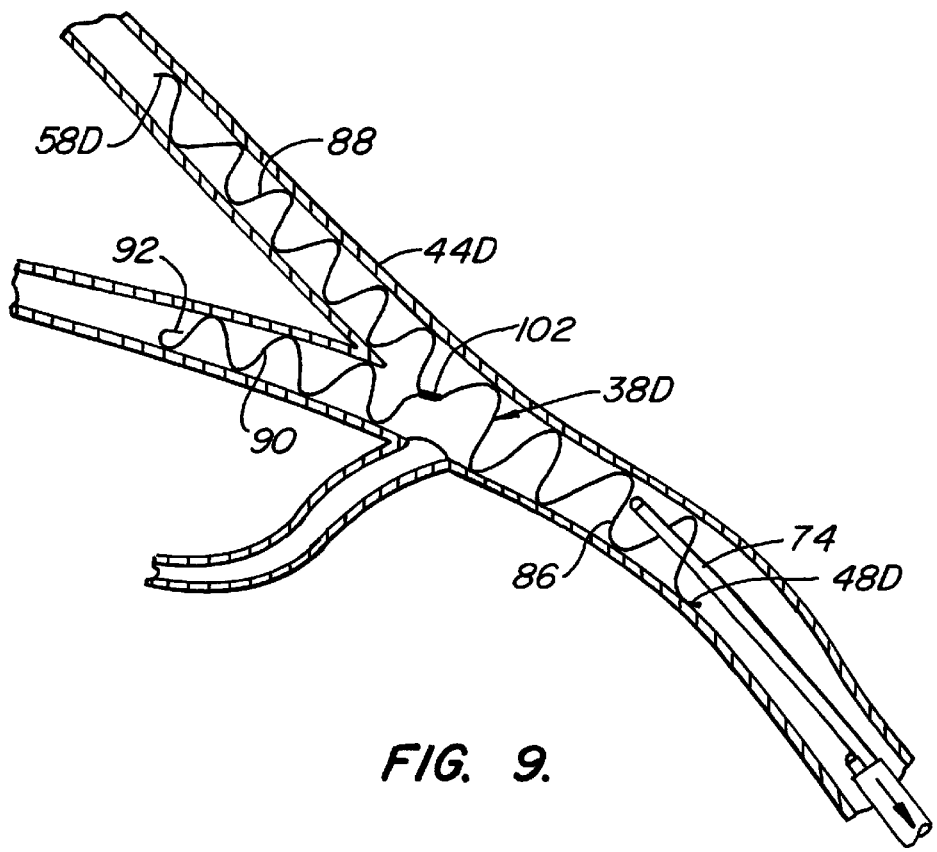
FIG. 9 shows the stent of FIG. 8 deployed in the vessel and the withdrawal of the catheter.

FIG. 7 illustrates distal catheter portion 34D with balloon 36D in a collapsed state, stent 38D wrapped around both balloon 36D and distal portion 34D, and showing the outline of a branched vessel 44D shown in dashed lines. Again, as with FIGS. 2A–2F, graft material is not shown for ease of illustration. However, as with the embodiments of FIGS. 1–4, graft material is typically used with stent 38D. Of course other types of stents, other than the coiled bifurcated stent shown in FIG. 6, could be used as well. The placement of stent 38D occurs in substantially the same fashion as can occur with the straight stent described above. The main difference is that proximal ends 48D and 92 of stent 38D are both released using push wires 30D while distal stent end 58D is released by the partial inflation of balloon 36D. FIG. 8 illustrates the result of having gone through the stent end release cycle, that is typically partial inflation, which releases stent end 58D, deflation and then the full inflation and release of stent ends 48D, 92. After stent 38D has been expanded, distal catheter portion 34D and balloon 36D therewith are removed from the bifurcated target site as suggested in FIG. 9. Again, graft material is not shown for clarity of illustration. As with the above embodiments, graft material may not be, but often is, used with the stent or other prosthesis.

Figure 10:
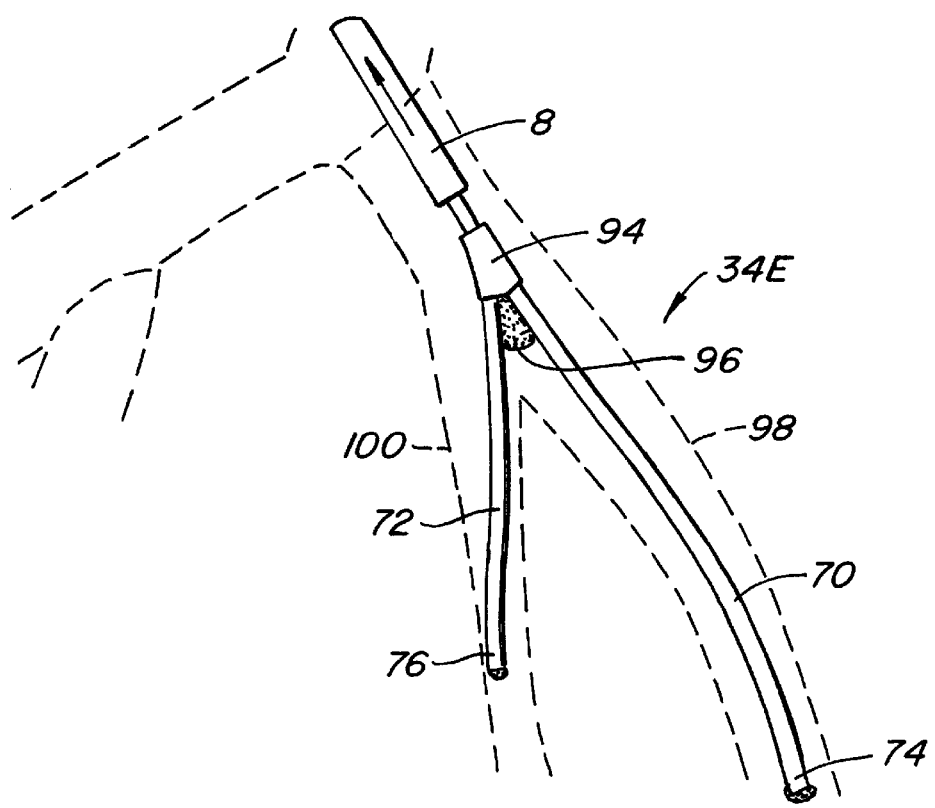
FIG. 10 shows a bifurcated catheter with a spring member used to keep the catheter shaft arms apart.

FIG. 10 illustrates a distal catheter portion 34E similar to that shown in FIG. 5 in which the first and second arms 70, 72 are biased outwardly at their junction 94 by a biasing element 96 which tends to separate arms 70, 72 from one another. Biasing element may be made of a variety of materials, such as a leaf spring or, as illustrated, a triangular section of a resilient spongy material such as silicone or polyurethane. Using biasing element 96 helps to ensure arms 70, 72 are directed down different vascular segments 98, 100. To do so distal catheter portion 34E is typically housed within sheath 8 until just above the target site. At that point, distal portion 34E is extended out through the open distal end of introducer sheath 8 permitting arms 70, 72 to move freely into vascular segments 98, 100. This movement may be aided using guidewires 24D in addition to biasing element 96.

Modifications and variation may be to the above-described catheter assembly and method may be made. For example, it may not be necessary to only partly inflate the balloon as indicated in FIG. 2B; rather, it may be desired to fully inflate the balloon to release distal stent end 58 from distal stent end holder 56. Also, it may not be necessary to deflate the balloon after the full or partial inflation of the balloon as shown in FIG. 2C. In a preferred embodiment, a coiled stent is placed in torqued compression onto the catheter shaft and balloon. Other types of radially expanding stents, which may or may not be self-expanding, can be used as well. For example, tubes of stent material having numerous axially extending slits which permit the tube to be expanded radially in a diamond-like pattern using the balloon can be used. The stent could also be made of a temperature-sensitive shape-memory material. In the preferred embodiment, balloon 36 is necessary to expand graft 40 from its reduced-diameter state of FIG 1B to its expanded-diameter state of FIG. 4A; graft material may be used which does not require a balloon to place it into its fully expanded condition. In the preferred embodiment, graft 40 is an expandable, porous PTFE graft material such as that available from IMPRA, Baxter, W. L. Gore or Atrium. Other types of graft material, such as polyester or polyurethane, can be used. Instead of mechanically releasing proximal end 48 of stent 38, the proximal end can be held and selectively released by electrolytic methods as shown in U.S. Pat. No. 5,122,136 to Guglielmi, et al. Distal stent end 58 could be releasably coupled to catheter shaft 18 for release by inflation of balloon 36 by other than holder 56, such as through a releasable or breakable tether, a clip or other fastener, adhesive or other releasable or breakable structure. The holding and selective release of proximal stent end 48 could be by using a range of conventional or unconventional holders; for example, the distal end of sheath 8 could be left to cover the proximal end 52 of balloon 36 during the initial inflation of balloon and then pulled back to uncover the proximal balloon end for the subsequent inflation of the balloon. Pull or push wires could be used to actuate a catch to release proximal stent end 48. Conventional techniques, such as those shown in U.S. Pat. Nos. 5,372,600; 5,476,505; 5,683,451; 5,443,500; 4,913,141; 5,246,445; 5,360,401; 5,201,757; 4,875,480; 4,848,343; 4,732,152; and 4,665,918, and those shown in WO 97/07756 and WO 94/16629, may also be used to release proximal stent end 48.

Bifurcated embodiments have been shown illustrating use of a single balloon. If desired, a number of separate balloons could be used instead of a single balloon. For example, three separate balloons could be used, one for each branch of the stent. The three balloons could be all coupled to a single inflation lumen; in such case the three separate balloons would act similarly to the single balloon. However, if each balloon were separately inflatable, more than one of the stent ends could be released through the inflation of the various balloons. Stent 38D is shown with main portion 86 and first and second arms 88, 90 secured together at a common location 102. It may be desired to have, for example, second arm 90 be joined to a section of stent 38D between main portion 86 and first arm 88 by a sliding connection; this may be useful to help properly seat or orient the stent or a stent graft within the bifurcated vessel. First arm 88 is shown as a single continuous coil in FIG. 6. If desired, first arm 88 could include one or more separate sections of stent to create the first arm. Instead of having a single catheter split into two catheter arms, second arm 72 could actually be a separate catheter extending through the interior of catheter shaft 18D; this would facilitate inflating a balloon associated with the second arm separately from the one or more other balloons associated with the main portion of the catheter shaft and the first arm. It may also permit the second arm of the catheter shaft to move longitudinally relative to the main catheter shaft and the first arm of the catheter shaft.

FIG. 11 illustrates a stent blank 104 used to create a coiled stent similar to that shown in FIG. 4E. Stent blank 104 includes a main body portion 106 and first and second end portions 108. Main body portion 106 includes side edge or rail elements 110 connected by connector or rung elements 112. Rung elements 112 are, as shown in FIG. 11, at an angle to rail elements 110 so that when stent blank 104 is formed into a coiled stent and tightly wrapped about an introducer catheter, such as in FIG. 17A, rung elements 112 are axially-extending so that they lie flat for a tighter wrap.

End portions 108 are thinner and thus more flexible than main body portion 106. In addition, end portions 108 have an inwardly tapering portion 114 terminating at a blunt tip 115. The shape of end portions 108 and the lessened stiffness of the end portions, compared to body portion 106, help to prevent tissue trauma during use. This type of coiled stent in which the end portions 108 are less stiff than the main body portion 106 can find particular utility in stabilizing a traumatic injury site within a patient, such as in the case of a dissection, flap or false lumen. End portion 108 could also be more stiff than main body portion; this embodiment may be useful, for example, when treating occlusive disease on either side of a branch vessel.

FIG. 12 illustrates a stent blank 104A similar to stent blank 104 of FIG. 11 but in which main body portion 106A has three different radial stiffnesses. That is, main body portion 106A has a first, central longitudinal section 116 of a first, greater stiffness, and second and third longitudinal sections 118, 120 on either side of first section 116. Sections 118, 120 are successively thinner and thus have successively lower radial stiffness when stent blank 104A is formed into a coiled stent. End portion 108A acts as the fourth longitudinal section with the least radial stiffness of any of the sections in this embodiment. Instead of a set of generally discrete radial stiffness, the radial stiffness could vary continuously along at least part of the length of stent blank 104A, and then along the resulting stent body.

In addition to providing less traumatic end portions 108, 108A, a coiled prosthesis formed from either of stent blanks 104, 104A, when uncoiling, will have a tendency to open up first in the center, because of the greater stiffness at the center, followed by the ends. This helps to reduce the degree to which the end portions 108, 108A are dragged along the surface of the vessel or other hollow body structure as the prosthesis is released.

FIGS. 13, 14, 15 and 15A illustrate four stent graft embodiments 122, 122A, 122B, 122C. Stent graft 122 includes a ladder-type coiled stent formed from stent blank 104 and covered with tubular graft material 124. Graft material 124 is preferably porous PTFE or ePTFE. The ends 126 of graft material 124 are sealed, or for example, by using an adhesive or by placing a suitable heat seal material, such as FEP (fluorinated ethylene propylene) or other thermoplastic materials, between the layers of the graft material 124 and applying heat and pressure. The porous nature of the graft material permits sealing in this manner in spite of the inert nature of PTFE. In addition, a direct bond of the PTFE to itself, via a process known as sintering, may be employed. Other methods for sealing ends 126 could also be used. Coiled stent graft 122 includes a number of spaced apart turns 128 defining a generally helical gap 130 therebetween. The helical nature of the gap 130 is believed to help prevent restenosis in two ways. First, the helical nature of stent graft 122 and of gap 130 is expected to help induce a blood flow pattern which helps to reduce plaque build up. Second, if plaque build up does occur along the edges of helical gap 13, the helical nature of gap 13 is expected to induce quicker and more uniform endothelialization which reduces the likelihood of restenosis.

The average width of helical gap 130 is equal to about 0% to 1200% of the average width of turns 128. More typically the average width of gap of 130 is about 50% to 800% of the average width of turns 128 when stent graft 122 is deployed. Also, stent graft 122 has a generally constant pitch except at its central region. The pitch of a central turn 132 of stent graft 122 is substantially greater than the pitch of its adjacent turns 128 to accommodate placement of stent graft 122 at the intersection of a main or first vessel and a branching vessel as will be discussed in more detail with reference to FIGS. 17A–17C.

FIG. 14 illustrates a stent graft 122A in which a central turn 132A also has an increased pitch as opposed to adjacent turns 128A. However, the turns on one side of central turn 132A have a larger fully-expanded diameter than turns on the other side to accommodate transition between smaller and larger diameter vessels.

Figure 15:
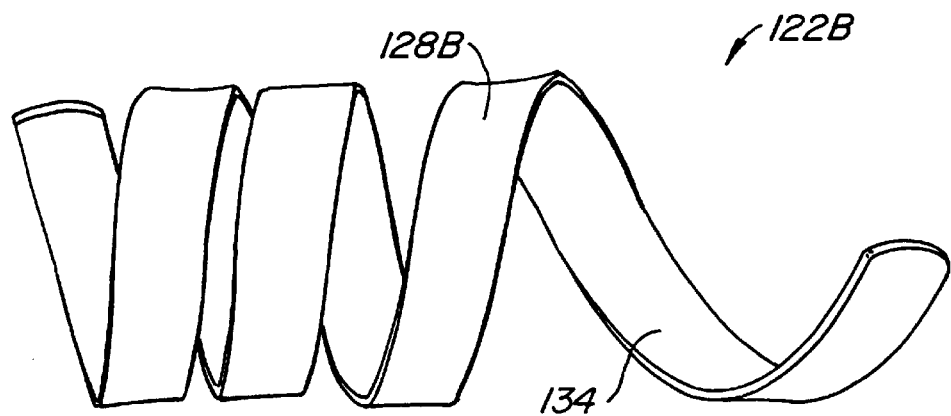
FIG. 15 illustrates an alternative embodiment to the stent graft of FIG. 13 in which the stent graft has a large expanded diameter and also has the one turn with the greater pitch at one end of the stent graft.

FIG. 15 illustrates a stent graft 122B designed for placement with the end turn 134 having a substantially greater pitch than its adjacent turn 128B. Stent graft 122B is used when one end of the stent graft is to be positioned at the intersection and main and branching vessels so that the stent graft extends to one side of the intersection as opposed to both sides as in the embodiments of FIGS. 13 and 14. FIG. 15A illustrates stent graft 122C, which may be used at locations other than bifurcations, having generally uniformly spaced turns 128C.

Figure 13:
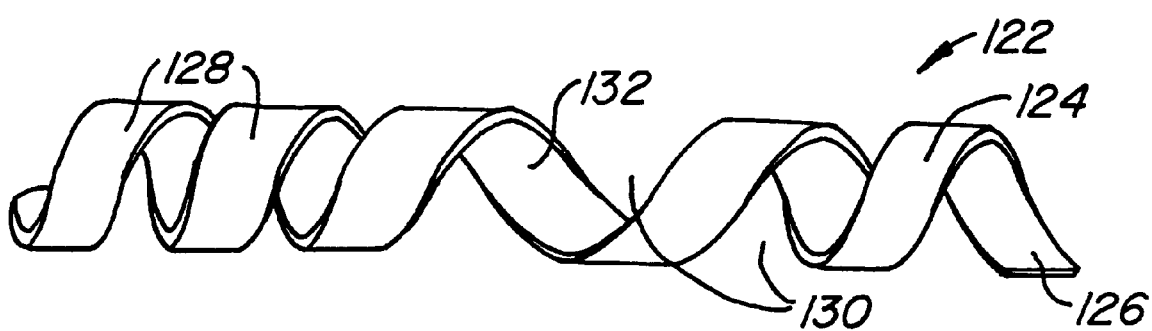
FIG. 13 illustrates a stent graft in a radially expanded condition, the stent graft including a stent similar to that shown in FIG. 11 covered with a sleeve of porous graft material, the stent graft having a central turn with a greatly increased pitch for placement at a branching intersection.
Figure 16A:
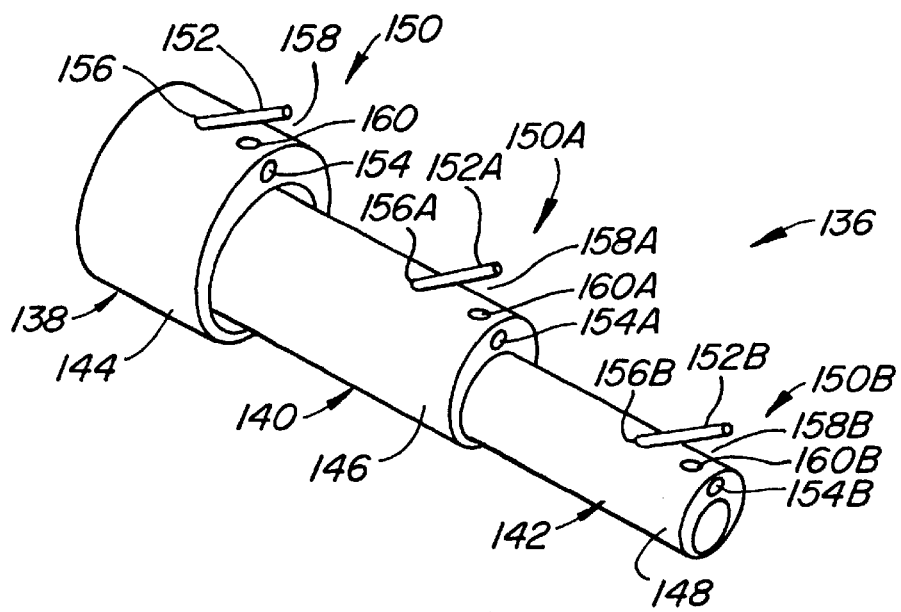
FIG. 16A is an overall view of the distal end of a three-shaft deployment catheter used to deploy the stent grafts of FIGS. 13–15.
Figure 16B:
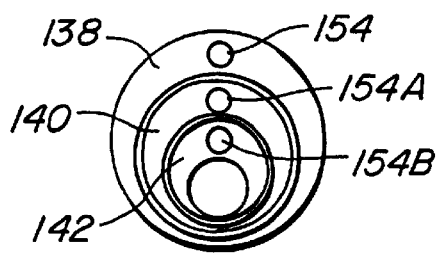
FIG. 16B is an end view of the shafts of 16A.
Figure 17A:
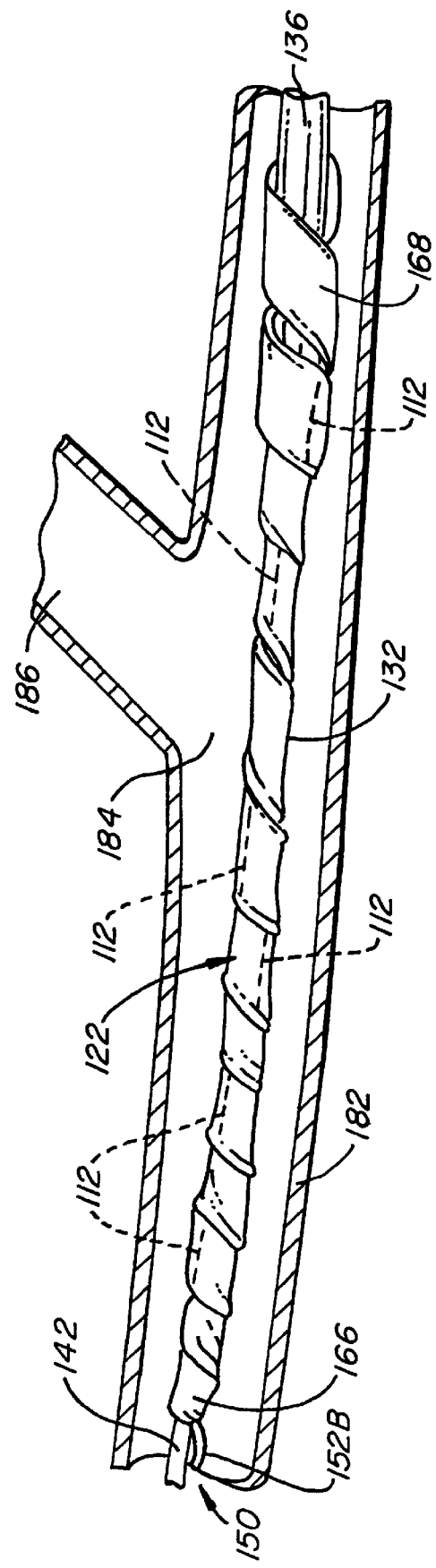
FIG. 17A illustrates the stent graft of FIG. 13 tightly wrapped about the distal end of the catheter of FIGS. 16A and 16B and placed within a vessel with the intermediate portion of the stent graft at the intersection of the main and branching vessels.

FIGS. 16A–16B illustrate a catheter 136 used for deploying the stent grafts of FIGS. 13 and 14. Catheter 136 includes outer, intermediate and inner rotating, telescoping shafts 138, 140, 142 each having a distal end 144, 146, 148. Each of the shafts has a prosthesis portion holder 150, 150A, 150B at its distal end 144, 146, 148. Prosthesis portion holders 150, 150A, 150B include pull wires 152, 152A, 152B which pass along axially-extending lumens 154, 154A, 154B formed in the body of shafts 138, 140, 142, out of exit holes 156, 156A, 156B, across gaps 158, 158A, 158B and back into reinsertion openings 160, 160A, 160B. Pull wires 152, 152A, 152B pass through and engage different portions of, for example, stent graft 122 and secure those portions of the stent graft to shafts 138, 140, 142. As shown in FIG. 17A, prosthesis portion holder 150B at distal end 148 of inner shaft 142 engages the distal end 166 of stent graft 122. Holders 150, 150A at distal ends 144, 144A of outer and intermediate shafts 138, 140 engage proximal end 168 and central turn 132 of stent graft 122, respectively. One or more of shafts 138, 140, 142 may be braided to enhance torquing stiffness to aid rotation.

Figure 16C:
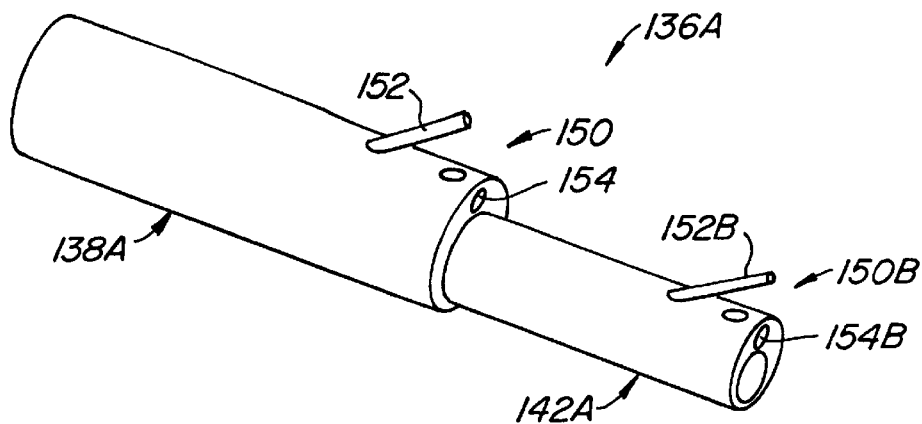
FIG. 16C is an embodiment similar to the catheter of FIG. 16A but including only inner and outer shafts.

FIG. 16C illustrates the distal end of a catheter 136A including only two shafts, outer shaft 138A and inner shaft 142A. Catheter 136A is typically used when placing an endoluminal prosthesis of the type which does not have a central turn with an increased pitch, such as those of FIGS. 15 and 15A, and thus does not need a catheter with an intermediate shaft.

Figure 16D:
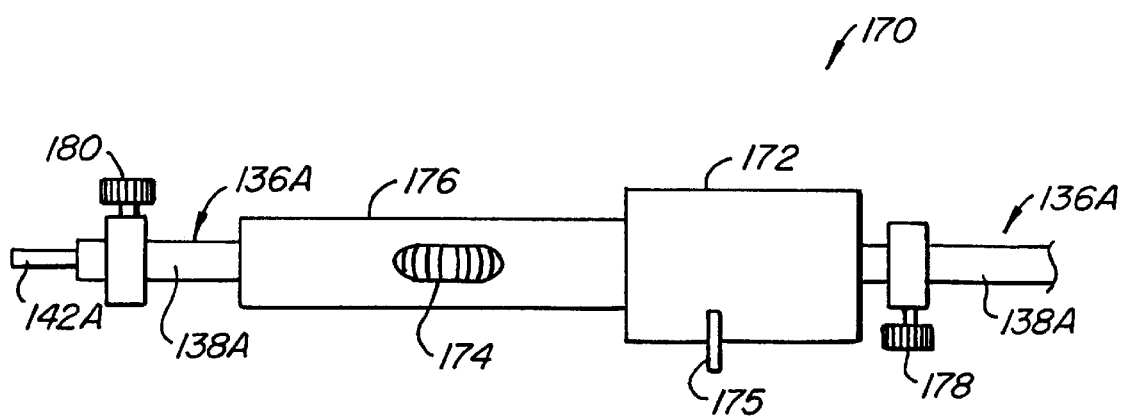
FIG. 16D illustrates a proximal end adapter mounted to the proximal end of the catheter of FIG. 16C.

FIGS. 16D illustrates, in a simplified form, aproximal end adapter 170 mounted to the proximal end of catheter 136A of FIG. 16C. Proximal end adapter 170 includes distal and proximal portions 172, 176 through which catheter 136A passes. Proximal end adapter 170 provides for the rotation of either or both shafts 138A, 142A through the manipulation of thumb wheel 174 mounted to portion 176. A flip lever 175 extends from distal portion 172 and is movable between secured and released positions to either secure shafts 138A, 142A to one another or to permit shafts 138A, 142A to move axially relative to one another. Pull wires 152, 152B are normally secured to their respective shafts 138A, 142A by deployment knobs 178, 180; pulling on deployment knobs 178, 180 releases pull wires 152, 152B, respectively to permit the pull wires to be pulled to release the endoluminal prosthesis from the appropriate holder 150, 150B.

Figure 16E:
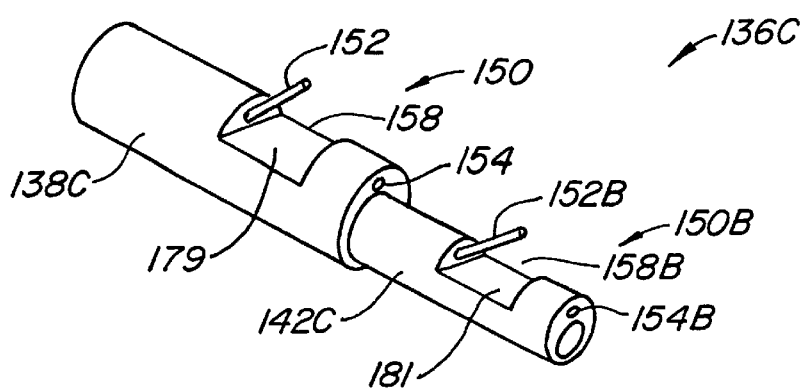
FIG. 16E illustrates an alternative embodiment of the catheter of FIG. 16C.
Figure 16F:
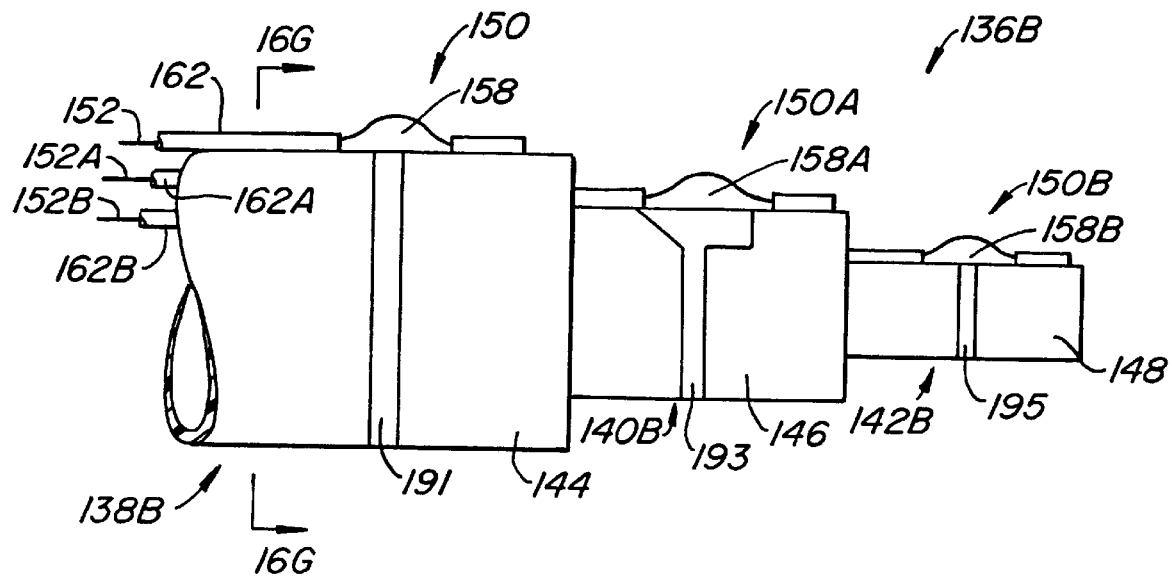
FIGS. 16F and 16G are simplified side and cross-sectional views of a further alternative embodiment of the catheter of FIGS. 16A and 16B.
Figure 16G:
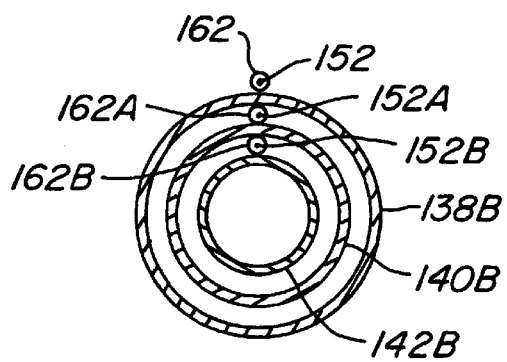

FIGS. 16F and 16G illustrate a further three-shaft embodiment of the invention similar to the three-shaft embodiment of FIGS. 16A and 16B. Instead of using lumens 154 to house pull wires 152, tubular members 162, 162A, 162B, typically hypotubes, could be secured to the outside of the shafts 138B, 140B, 142B. Gaps or breaks are provided at the distal ends of hypotubes 162, 162A, 162B to define the gaps 158, 158A, 158B.

Figure 18:
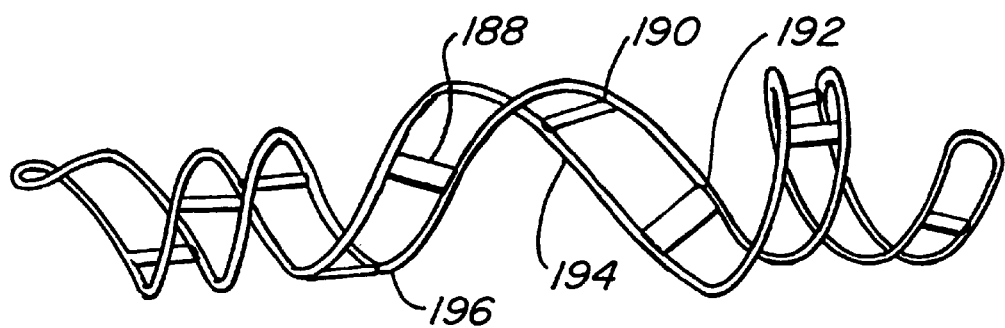
FIGS. 18 and 19 illustrate the placement of radiopaque marks at different positions along a coiled ladder-type stent having a central turn with a greatly increased pitch.
Figure 19:
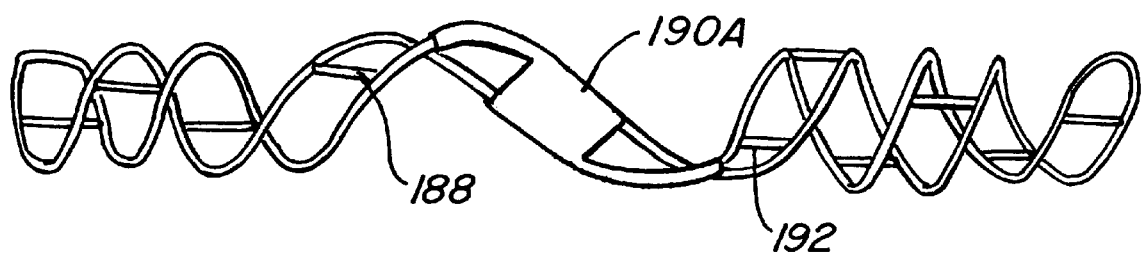

FIG. 17A shows stent graft 122 of FIG. 13 tightly wrapped about catheter 136. Distal end 166, proximal end 168 and central turn 132 of stent graft 122 are secured to distal ends 148, 144 and 146 of inner, outer and intermediate shafts 142, 138 140 by prosthesis portions holders 150. Stent graft 122 is housed within a main vessel 182 with central turn 132 aligned with the intersection 184 of main vessel 182 and branching vessel 186. To help ensure proper placement of central turn 132 at intersection 184, stent graft 122 has one or more remote visualization markers at or adjacent to turn 132. Radiopaque markers 188, 190 192 are shown in FIG. 18 at distal, intermediate and proximal portions of the central turn 194 of stent 196. Radiopaque markers may be shaped to provide information as to both location and orientation of stent 196 on the catheter. For example, radiopaque marker 190A of FIG. 19 has a broad central portion 190B extending between rail elements 110 and arm portions 190C extending along rail elements 110; this permits marker 190A to provide both location and orientation information about stent 196A. Orientation marker 190A is configured so that the viewer can determine whether the turn is facing the viewer or is away from the viewer based upon the marker's orientation. Various other marker shapes to provide both location and orientation can also be used.

Figure 20:
FIG. 20 illustrates one example of a radiopaque marker shaped to permit the determination of the orientation of the prosthesis as well as its location.

Radiopaque markers may also be used on the placement catheter itself. For example, radiopaque markers 191, 193, 195 are used on shafts 138B, 140B, 142B aligned with their respective holders 150, 150A, 150B, as shown in FIG. 16F, to indicate the location of the holders. Radiopaque marker 193 is shown to be configured as an orientation specific marker to help in the proper placement of the prosthesis. FIG. 20 illustrates the shape of an orientation-specific radiopaque marker 197 which could be placed, for example, on shafts 138, 140, 142 at one or more of the holders 150 of the embodiments of FIGS. 16A, 16C and 16E. Radiopaque or other remote visualization markers may also be used at other positions along the endoluminal prosthesis, such as at each end, or along the placement catheter.

FIG. 17B illustrates the release of proximal end 168 of stent graft 122 while FIG. 17C illustrates the subsequent release of distal end 166 of stent graft 122. It should be noted that central turn 132 remains secured to intermediate shaft 140 while the distal and proximal ends 166, 168 of stent graft 122 are released to ensure that the open region of central turn 122 remains facing intersection 184 to help ensure substantially unrestricted fluid flow between main vessel 182 and branching vessel 186. It should also be noted that prior to releasing the stent graft, the number of turns can be increased or decreased by the relative rotation of shafts 138, 140 and 142. Also, the length of stent graft 122 can be changed by the relative axial sliding motion among outer, intermediate and inner shafts 138, 140, 142. For example, instead of simply releasing proximal end 168 of stent graft 122 to the position shown in FIG. 17B, it may be desired to rotate outer shaft relative to intermediate shaft 140, keeping intermediate and inner shafts 140, 142 stationary so to unwind the proximal half of the stent graft to ensure that the stent graft is properly positioned prior to releasing the stent graft. Similarly, both outer shaft and inner shafts can be rotated while maintaining intermediate shaft stationary to create the expanded diameter condition of FIG. 17 prior to releasing any portion of the stent graft. In this way the physician can ensure that stent graft 122 is properly positioned, especially with respect to central turn 132. If necessary or desired, intermediate shaft 140 could be, for example, rotated relative to outer and inner shafts 138, 142 to help properly position or reposition central turn 132.

FIG. 17A also shows how by properly selecting the angle of connector elements 112 relative to side elements 110 for a placement catheter of a particular outside diameter, connector elements 112, indicated by dashed lines in FIG. 17A, will lie generally parallel to the axis of stent graft 122. This permits connector element 112 to lie closer to catheter 136, to provide a much smoother wrap when in its contracted, reduced-diameter state, than would result if connector elements were not generally parallel to the axis in such a state. This axial orientation can be contrasted with the off-axis orientation of connectors 112 when in the expanded diameter state of FIG. 17C. The smoother outer surface of stent graft 122 enhances the ease of insertion of the stent graft within a hollow body organ, such as blood vessel 182.

Figure 21:
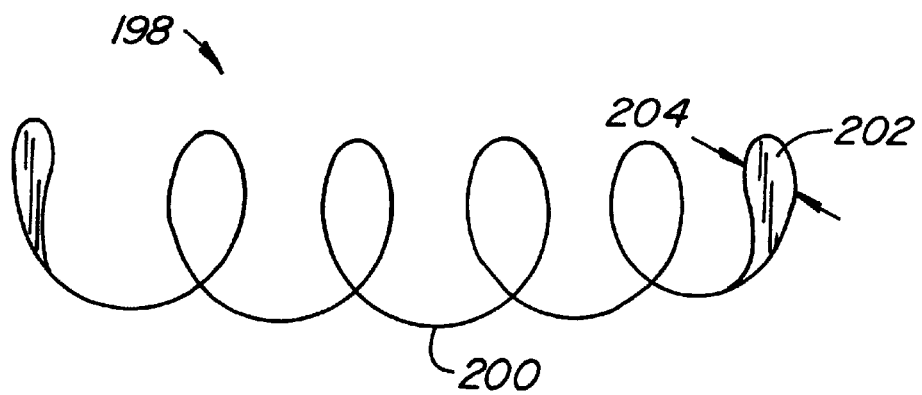
FIG. 21 illustrates a coiled prosthesis having enlarged blunt ends to help prevent tissue trauma.

As discussed above with reference to FIGS. 11 and 12, end portions 108, 108A of sent blanks 104, 104A are less stiff than main body portion 106, 106A, as well as having rounded, blunt tips 116, 116A. FIG. 21 illustrates a coiled prosthesis 198 in which the main body 200 has an average cross-sectional dimension of x while the enlarged blunt ends 202 have a maximum cross-sectional dimension 204 of 5 x to 25 x, and more preferably 5 x to 10 x. In one example main body 200 has a rectangular cross-sectional shape with a minimum width of 0.025 mm(0.001 in) and a maximum width of 1 mm (0.040 in); enlarged blunt end has a thickness of 0.025 mm (0.001 in) and a maximum cross-sectional dimension 204 of 1 cm (0.4 in). This configuration of the ends 202 of prosthesis 198 helps reduce trauma to the patient's tissue by making the ends of the prosthesis less stiff and also by providing a much greater surface area so to reduce the pressure exerted against the tissue, as opposed to what could be exerted by a coiled prosthesis having a constant cross-sectional dimension. The example of FIG. 21 could be modified so that ends 202, rather being solid, are made from loops of wire with open centers.

Modification and variation can be made to the above described inventions without departing from the subject of the inventions as defined in the following claims. For example, connectors 112 could be oriented perpendicular to rail elements 110, graft material 124 could be placed upon only a portion of the underlying stent or on only one side of the underlying stent. Placement catheter 136 could include fewer or additional telescoping rotatable shafts. The telescoping shafts may not need to be coaxial shafts slidable within or over one another; the telescoping shafts could be, for example, solid and/or tubular elongate members positioned side-by-side. Holders 150 could be constructed differently; for example, if the sequence of releasing the prosthesis is known it may be possible to use a single pull wire instead of three separate pull wires.

Any and all patents, applications, and printed publications referred to above are incorporated by reference.

What is claimed is:

1. A catheter assembly comprising:
 a catheter comprising first and second rotatable, telescoping shafts having first and second prosthesis portion holders, respectively;

an endoluminal prosthesis, capable of assuming a second, expanded-diameter state from a first, reduced-diameter state;

the prosthesis having first and second prosthesis portions releasably engageable with the first and second prosthesis portion holders, respectively; and the prosthesis comprising a coiled prosthesis, said prosthesis having a plurality of turns and a generally helical gap defined between said turns, whereby the prosthesis length and the number of turns of the coiled prosthesis can be changed by the relative longitudinal and rotary motion of the shafts.

2. The catheter assembly according to claim 1 wherein:
the first and second shafts have distal end portions, the first and second prosthesis portion holders being at said distal end portions; and
the endoluminal prosthesis at least partially surrounds the distal end portions.

3. The catheter assembly according to claim 1 wherein:
the catheter further comprises a third telescoping and rotatable shaft having a third prosthesis portion holder; and
the prosthesis has a third prosthesis portion releasably engageable with the third prosthesis portion holder.

4. The catheter assembly according to claim 3 wherein the second shaft is housed between the first and third shafts.

5. The catheter assembly according to claim 3 wherein:
the pitch of at least one turn at the second prosthesis portion is greater than the pitch of adjacent turns so to promote substantially unrestricted fluid flow between a first vessel, housing the prosthesis, and a branching vessel when the second prosthesis portion is at an intersection of the first and branching vessels; and
the second prosthesis portion is at a central region of the endoluminal prosthesis.

6. The catheter assembly according to claim 3 wherein the first and third prosthesis portions assume different diameters when the prosthesis is in the second, expanded-diameter state so to accommodate a change in vessel diameter.

7. The catheter assembly according to claim 1 wherein the prosthesis comprises a series of spaces, at least one of the spaces being substantially larger than an adjacent space to promote substantially unrestricted fluid flow between a first vessel housing the prosthesis and a branching vessel when the second prosthesis portion is at an intersection of the first and branching vessels.

8. The catheter assembly according to claim 1 wherein the prosthesis comprises a coiled stent graft, said stent graft having a plurality of turns and a generally helical gap defined between said turns.

9. The catheter assembly according to claim 8 wherein the coiled stent graft is a self-expanding coiled stent graft.

10. The catheter assembly according to claim 8 wherein the pitch of at least one turn at the second prosthesis portion is greater than the pitch of adjacent turns so to promote substantially unrestricted fluid flow between a first vessel housing the prosthesis and a branching vessel when the second prosthesis portion is at an intersection of the first and branching vessels.

11. The catheter assembly according to claim 1 further comprising a remotely viewable marker on at least one of the second prosthesis portion holder and the second portion of the prosthesis to aid placement of the prosthesis at an intersection of a branching vessel with a first vessel.

12. The catheter assembly according to claim 11 wherein the marker is an orientation marker so to provide information on both position and orientation of the second prosthesis portion.

13. The catheter assembly according to claim 1 wherein the prosthesis comprises a coiled stent having distal end regions.

14. The catheter assembly according to claim 13 wherein said distal end regions are substantially less stiff than the remainder of the coiled stent.

15. The catheter assembly according to claim 14 wherein said distal end regions each have an inwardly-tapering portion with a blunt tip, a longitudally-extending length and a laterally-extending width, and wherein said length is greater than said width.

16. The catheter assembly according to claim 13 wherein said distal end portions each have an inwardly-tapering portion with a blunt tip and a longitudinally-extending length and a laterally-extending width, and wherein the length is greater than the width.

17. The catheter assembly according to claim 13 wherein said coiled stent has first, second and third longitudinal sections each having a different radial stiffness.

18. The catheter assembly according to claim 13 wherein the coiled stent comprises a coiled ribbon of material with its width substantially greater than its thickness.

19. A catheter assembly comprising:
a catheter comprising first and second rotatable, telescoping shafts having first and second prosthesis portion holders, respectively;
an endoluminal prosthesis, capable of assuming a second, expanded-diameter state from a first, reduced-diameter state, the prosthesis comprising a self-expanding coiled stent graft, said stent graft having a plurality of turns and a generally helical gap defined between said turns;
the prosthesis having first and second prosthesis portions releasably engageable with the first and second prosthesis portion holders, respectively; and
the pitch of at least one turn at the second prosthesis portion being greater than the pitch of adjacent turns so to promote substantially unrestricted fluid flow between a first vessel housing the prosthesis and a branching vessel when the second prosthesis portion is at an intersection of the first and branching vessels.

20. The catheter assembly according to claim 19 wherein the second prosthesis portion is at an end of the coiled stent graft.

21. The catheter assembly according to claim 19 wherein:
the catheter shaft further comprises a third telescoping and rotatable shaft having a third prosthesis portion holder, and
the stent graft has a third prosthesis portion releasably engageable with the third prosthesis portion holder.

22. The catheter assembly according to claim 21 wherein the second shaft is housed between the first and third shafts.

23. The catheter assembly according to claim 21 wherein the second prosthesis portion is at a central region of the stent graft.

24. The catheter assembly according to claim 21 further comprising first, second and third remotely viewable marker elements at spaced-apart positions on the second prosthesis portion of the stent graft so to aid proper placement of said second prosthesis portion at the intersection of the first and branching vessels.

25. A catheter assembly comprising:
a catheter comprising first and second rotatable, telescoping shafts having first and second prosthesis portion holders, respectively;
an endoluminal prosthesis, capable of assuming a second, expanded-diameter state from a first, reduced-diameter state, the prosthesis comprising a coiled stent, the coiled stent comprising a coiled ribbon of material with its width substantially greater than its thickness; and the prosthesis having first and second prosthesis portions releasably engageable with the first and second prosthesis portion holders, respectively.

26. The catheter assembly according to claim 25 further comprising a tubular graft material surrounding the coiled ribbon of material to create a coiled stent graft in which adjacent turns define gaps therebetween.

27. The catheter assembly according to claim 26 wherein the gaps and the turns of the coiled stent graft both have average longitudinal dimensions, the average longitudinal dimension of said gaps being about 0% to 1200% of the average longitudinal dimension of the turns of the coiled stent graft.

28. The catheter assembly according to claim 27 wherein the average longitudinal dimension of the gaps is about 50% to 800% of the average longitudinal dimension of the turns of the coiled stent graft.

29. The catheter assembly according to claim 25 wherein the coiled ribbon of material has edge elements separated by connector elements.

30. A catheter assembly comprising:
   a catheter comprising first and second rotatable, telescoping shafts having first and second prosthesis portion holders, respectively, said first shaft being a tubular shaft housing said second shaft therein;
   a coiled endoluminal prosthesis, having a plurality of turns and a generally helical gap defined between said turns, capable of assuming a second, expanded-diameter state from a first, reduced-diameter state;
   the prosthesis having first and second prosthesis portions releasably engageable with the first and second prosthesis portion holders, respectively;
   whereby the length and the number of turns of the coiled endoluminal prosthesis can be changed by relative longitudinal and rotary motion of the shafts.

31. A method for placing an endoluminal prosthesis within a body comprising:
   introducing a distal portion of a catheter assembly at a chosen position within a body, the distal catheter portion comprising a coiled endoluminal prosthesis wound about a catheter shaft the prosthesis having a plurality of turns and being capable of assuming a second, expanded-diameter state from a first, reduced-diameter state, said turns having spaces therebetween when in the second state, the pitch of at least one turn being greater than the pitch of adjacent turns when in the second state, the prosthesis releasably connected to the catheter shaft at a first position along the prosthesis at the at least one turn and at a second position along the prosthesis, the second position being spaced-apart from the first position;
   locating said at least one turn at an intersection of a first vessel and a branching vessel;
   releasing the prosthesis from the catheter,
   maintaining the first position of the prosthesis at the intersection; and
   the locating and maintaining steps being carried out so to keep the intersection substantially unobstructed to enhance fluid flow between the first and branching vessels with the prosthesis in its second, expanded-diameter state.

32. The method according to claim 31 wherein said introducing step is carried out with said at least one turn being at an end of said prosthesis.

33. The method according to claim 31 wherein:
   the introducing step is carried out with said at least one turn being at a central portion of said prosthesis, the second position and a third position along the prosthesis being on opposite sides of the first position;
   the introducing step is carried out using a catheter shaft comprising outer, intermediate and inner rotatable, telescoping shafts releasably connected to the second, first and third positions, respectively; and
   the releasing step is carried out by releasing the third position and then the first position from the catheter shaft.

34. The method according to claim 31 wherein the releasing step comprises:
   releasing the second position of the prosthesis from the catheter permitting at least a portion of the prosthesis to detach; and
   releasing the remainder of the prosthesis, including the first position, from the catheter shaft permitting the remainder of the prosthesis to detach.

35. The method according to claim 31 wherein the introducing step is carried out using a catheter shaft comprising first and second rotatable, telescoping shafts, said first and second positions of the prosthesis releasably connected to the first and second telescoping shafts, respectively.

36. The method according to claim 35 further comprising the step of longitudinally moving at least one of the first and second telescoping shafts relative to the other to selectively adjust the length of the prosthesis.

37. The method according to claim 36 further comprising the step of rotating at least one of the first and second telescoping shafts relative to the other to selectively adjust the number of turns of the prosthesis.

38. A method for placing an endoluminal prosthesis within a body comprising:
   introducing the distal portion of a catheter assembly at a chosen position within a body, the distal catheter portion comprising a coiled endoluminal prosthesis wound about first and second rotatable, telescoping shafts, the prosthesis having a plurality of turns and being capable of assuming a second, expanded-diameter state from a first, reduced-diameter state, said turns having spaces therebetween when in the second state, the prosthesis releasably connected to the first and second shafts at first and second positions along the prosthesis, the second position being spaced-apart from the first position;
   locating said prosthesis at a target site;
   selectively adjusting the number of turns of the prosthesis by rotating at least one of the shafts relative to the other;
   selectively adjusting the length of the prosthesis by longitudinally moving at least one of the shafts relative to the other;
   releasing the prosthesis from the shafts; and
   removing the shafts from the body.

39. The method according to claim 38 wherein said introducing step is carried out with said first and second positions at distal ends of said prosthesis and releasably connected to distal ends of the first and second shafts.

40. The method according to claim 38 wherein the releasing step comprises:

releasing the second position of the prosthesis from the second shaft permitting at least a portion of the prosthesis to expand; and releasing the first position of the prosthesis from the first shaft permitting the remainder of the prosthesis to expand.

41. The method according to claim 38 wherein the selectively adjusting steps are carried out so that the prosthesis is placed in its expanded-diameter state prior to the releasing step so that the proper placement of the prosthesis can be confirmed prior to said releasing step.

42. A catheter assembly comprising:

a catheter comprising first and second rotatable, telescoping shafts having first and second prosthesis portion holders, respectively;

an endoluminal prosthesis, capable of assuming a second, expanded-diameter state from a first, reduced-diameter state;

the prosthesis having first and second prosthesis portions releasably engageable with the first and second prosthesis portion holders, respectively;

the first and second shafts having distal end portions, the first and second prosthesis portion holders being at said distal end portions; and the endoluminal prosthesis at least partially surrounding the distal end portions.

43. A catheter assembly comprising:

a catheter comprising first and second rotatable, telescoping shafts having first and second prosthesis portion holders, respectively;

an endoluminal prosthesis, capable of assuming a second, expanded-diameter state from a first, reduced-diameter state;

the prosthesis having first and second prosthesis portions releasably engageable with the first and second prosthesis portion holders, respectively; and a remotely viewable marker on at least one of the second prosthesis portion holder and the second portion of the prosthesis to aid placement of the prosthesis at an intersection of a branching vessel with a first vessel, the marker being an orientation marker so to provide information on both position and orientation of the second prosthesis portion.

44. A catheter assembly comprising:

a catheter comprising first and second rotatable, telescoping shafts having first and second prosthesis portion holders, respectively;

an endoluminal prosthesis, capable of assuming a second, expanded-diameter state from a first, reduced-diameter state;

the prosthesis comprising a coiled stent having distal end regions, said distal end regions being substantially less stiff than the remainder of the coiled stent; and the prosthesis having first and second prosthesis portions releasably engageable with the first and second prosthesis portion holders, respectively.

45. A catheter assembly comprising:

a catheter comprising first and second rotatable, telescoping shafts having first and second prosthesis portion holders, respectively;

an endoluminal prosthesis, capable of assuming a second, expanded-diameter state from a first, reduced-diameter state, the prosthesis comprising a coiled stent, said distal end regions each having an inwardly-tapering portion with a blunt tip and a longitudinally-extending length and a laterally-extending width, and wherein the length is greater than the width; and the prosthesis having first and second prosthesis portions releasably engageable with the first and second prosthesis portion holders, respectively.

46. A catheter assembly comprising:

a catheter comprising first and second rotatable, telescoping shafts having first and second prosthesis portion holders, respectively;

an endoluminal prosthesis, capable of assuming a second, expanded-diameter state from a first, reduced-diameter state, the prosthesis comprising a coiled stent, said coiled stent having first, second and third longitudinal sections each having a different radial stiffness; and the prosthesis having first and second prosthesis portions releasably engageable with the first and second prosthesis portion holders, respectively.

* * * * *